US012780914B2

(12) United States Patent
Collarini et al.

(10) Patent No.: US 12,780,914 B2
(45) Date of Patent: Nov. 3, 2026

(54) ANTI-TIGIT ANTIBODY AND METHODS OF USE THEREOF

(71) Applicant: CRYSTAL BIOSCIENCE INC., Emeryville, CA (US)

(72) Inventors: Ellen Collarini, Oakland, CA (US); Shelley Izquierdo, Berkeley, CA (US); Christel Iffland, Arlington, MA (US); William Don Harriman, Alameda, CA (US)

(73) Assignee: CRYSTAL BIOSCIENCE INC., Emeryville, CA (US)

( * ) Notice: Subject to any disclaimer, the term of this patent is extended or adjusted under 35 U.S.C. 154(b) by 833 days.

(21) Appl. No.: 18/015,319

(22) PCT Filed: Jun. 29, 2021

(86) PCT No.: PCT/US2021/039664

§ 371 (c)(1),
(2) Date: Jan. 9, 2023

(87) PCT Pub. No.: WO2022/031387

PCT Pub. Date: Feb. 10, 2022

(65) Prior Publication Data

US 2023/0265187 A1 Aug. 24, 2023

Related U.S. Application Data

(60) Provisional application No. 63/061,533, filed on Aug. 5, 2020.

(51) Int. Cl.
*C07K 16/28* (2006.01)

(52) U.S. Cl.
CPC ...... *C07K 16/2803* (2013.01); *C07K 2317/24* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2011/0256134 | A1 | 10/2011 | Bunting et al. |
| 2016/0355589 | A1 | 12/2016 | Williams et al. |
| 2018/0105600 | A1 | 4/2018 | Pons et al. |
| 2020/0040082 | A1 | 2/2020 | Piasecki et al. |
| 2020/0062859 | A1 | 2/2020 | Piasecki et al. |

FOREIGN PATENT DOCUMENTS

| | | | |
|---|---|---|---|
| WO | WO 2020/098734 | A1 | 5/2020 |
| WO | WO 2020/144178 | A1 | 7/2020 |

OTHER PUBLICATIONS

Brown et al. Tolerance to Single, but Not Multiple, Amino Acid Replacements in Antibody VH, CDR2. J Immunol (1996) 156 (9): 3285-3291, DOI: 10.4049/jimmunol. 156.9.3285 (Year: 1996).*

(Continued)

*Primary Examiner* — Amy E Juedes
*Assistant Examiner* — Hilary Ann Petrash
(74) *Attorney, Agent, or Firm* — James S. Keddie; Bozicevic, Field & Francis LLP

(57) ABSTRACT

The present disclosure provides antibodies that specifically bind to TIGIT. The antibodies find use in a variety of treatment, diagnostic, and monitoring applications, which are also described. For example, the antibody may be used to treat a patient for cancer, particularly a patient is also being treated or has been treated with an immune checkpoint inhibitor, e.g., a PD-1/PD-L1 inhibitor.

18 Claims, 9 Drawing Sheets

Specification includes a Sequence Listing.

(56) References Cited

OTHER PUBLICATIONS

Chauvin and Zarour (2020) TIGIT in cancer immunotherapy. J for Immuno Therapy of Cancer; 8, e000957, doi: 10.1136/jitc-2020-000957 (Year: 2020).*
Clark et al. Influence of canonical structure determining residues on antibody affinity and stability. Journal of Structural Biology 185 ( 2014) 223-227, DOI: 10.1016/j.jsb.2013.08.009201 (Year: 2014).*
Cui et al. (2025) TIGIT in cancer: from mechanism of action to promising immunotherapeutic strategies. Cell Death and Disease 16: 664, https://doi.org/10.1038/s41419-025-07984-4 (Year: 2025).*
Culang et al. (2013) The structural basis of antibody-antigen recognition. Front. in Immun. 2013. vol. 4, Article 302, pp. 1-13. DOI: 10.3389/fimmu.2013.00302 (Year: 2013).*
Drug Target Review (2025) Why TIGIT cancer therapies work in monkeys but not in humans. Nov. 2025, https://www.drugtargetreview.com/news/191003/why-tigit-cancer-therapies-work-in-monkeys-but-not-humans/ (Year: 2020).*
Jia et al. (2018) TIGIT expression positively associates with NK cell function in AML patients. Blood 132(Supplemental 1):5250, https://doi.org/10.1182/blood-2018-99-113578 (Year: 2018).*
Kaur and Salunke (2015) Antibody promiscuity: understanding the paradigm shift in antigen recognition. IUBMB Life, 67: 498-505, https://doi.org/10.1002/iub.1397 (Year: 2015).*
Kapingidza et al. 2020. Antigen-Antibody Complexes. Vertebrate and Invertebrate Respiratory Proteins, Lipoproteins and other Body Fluid, CH 19, pp. 465-484 (Year: 2020).*
Manallac (2025) Four therapies hanging on in troubled TIGIT space. BioSpace,https://www.biospace.com/drug-development/four-therapies-hanging-on-in-troubled-tigit-space (Year: 2025).*
Qi et al. (2022) CBL-B inhibition showed differentiated effects in a mixed lymphocyte reaction versus other immune-oncology targeted approaches. J Immunother Cancer; 10(Suppl 2): A1-A1603, https://doi.org/10.1136/jitc-2022-SITC2022.1354 (Year: 2022).*
Rawla and Barsouk. Epidemiology of gastric cancer: global trends, risk factors and prevention. Gastroenterology Rev 2019; 14 (1): 26-38, https://doi.org/10.5114/pg.2018.80001 (Year: 2019).*

* cited by examiner

A

```
                                 LC CDR1                  LC CDR2                         LC CDR3
                   10        20        30        40        50        60        70        80        90        100       110
43352p1.A11.seq    QSVLTQPPSASGTPGQRVTISCSGISAKIGN-NYVSWY------QQLPGTAPKLLIYFNNQRPSGVPDRFSGSKSGTSASLAISGLQSEDEADYYCASWDDSLNAWLFGGGTKLTVL
43352p1.D11.seq    QSVLTQPPSASGTPGQRVTISCSGISAKIGN-NYVSWY------QQLPGTAPKLLIYFNNQRPSGVPDRFSGSKSGTSASLAISGLQSEDEADYYCASWDDSLNAWLFGGGTKLTVL
43352p1.H08.seq    QSVLTQPPSASGTPGQRVTISCSGSRSNLGN-NLVYWY------QQLPGTAPKLLIYFNNERPSGVPDRFSGSKSGTSASLAISGVQSEDEADYYCATWDDSLNGWVFGGGTKLTVL
43586p1.1.A07.seq  QSVMTQPPSASGTPGQRVTISCSGSSSNIGTNRYVHWY------KQVPGTAPKLLIYGNHQRPSGVPDRFSGSKSGTSASLAISGLQSEDEADYYCAAWDGSLSGWVFGGGTKLTVL
43586p1.1.C02.seq  QSVLTQPPSASGTPGQRVTISCSGGSSNIGT-NYVSWY------QQLPGTAPKLLLYKEDQRPSGVPDRFSGSKSGTSASLAISGLQSEDEADYYCAnVDGSLRSWVFGGGTKLTVL
43586p1.1.G09.seq  QSVLTQPPSASGTPGQRVTISCSGSTSNIGTSRYVHWY------QHLPGTAPKLLIYLDSQRPSGVPDRFSASKSGTSASLAISGLQSEDEADYYCSAWDDSLSAWVFGGGTKLTVL
43586p1.1.H08.seq  QSVLTQPPSASGTPGQRVIISCSGSTSDIET-KYVSWY------QQLPGTAPKLLIYGNHQRPSGVPDRFSGSKSGTSASLAISGLQSEDEADYYCTAWDNTLKSWVFGGGTKLTVL
43586p1.2.A04.seq  QSVLTQPPSASGTPGQRVTISCSGSRSNVGD-HYVSWY------QQFPGTAPKLLIYANYQRPSGVPDRFSGSKSGTSASLAISGLQSEDEADHYCASWOASLNVWVFGGGTKLTVL
43586p1.2.B02.seq  QSVLTQPPSASGTPGQRVTISCSGSISNIET-KYVSWY------QQLPGTAPKLLIYNSDQRPSGVPDRFSGSKSGTSASLAISGLQSEDEADYYCVSWDASLKSWVFGGGTKLTVL
43586p1.2.B08.seq  QSVLTQPASASGTPGQRVTITCSGTISNIET-KYVSWY------QQLPGTAPKLLIYGNHQRPSGVPDRFSGSKSGTSASLAISGLQSEDEADYYCASWENDLKSWVFGGGTKLTVL
43586p1.2.C05.seq  QSVLTQPPSASGTPGQRVTISCSGSNFNIGT-KYLYWY------QQLPGTAPKLLIYLDSQRPSGVPDRFSTSKPGTSASLAISGLQSEDEADYYCALWDDHLHGWVFGGGTKLTVL
43586p1.2.C09.seq  QSVLTQPPSASGTPGQRVTISCSGSISNIET-KYVSWY------QQLPGTAPKLLIYNSDQRPSGVPDRFSGSKSGTSASLAISGLQSEDEADYYCVSWDASLKSWVFGGGTKLTVL
43586p1.2.C11.seq  QSVLTQPPSASGTPGQRVTISCSGSISNIET-KYVSWY------QQLPGTAPKLLIYNSDQRPSGVPDRFSGSKSGTSASLAISGLQSEDEADYYCVSWDASLKSWVFGGGTKLTVL
43586p1.2.C12.seq  QSVLTQPPSASGTPGQRVTISCSGTISNIEI-KYVSWY------QQLPGTAPKLLIYGNHQRPSGVPDRFSGSKSGTSASLAISGLQSEDEADYYCSSWENDLKSWVFGGGTKLTVL
43586p1.2.E01.seq  QSVLTQPPSASGTPGQRVTISCSGTISNIEI-KYVSWY------QQLPGTAPKLLIYGNHQRPSGVPDRFSGSKSGTSASLAISGLQSEDEADYYCSSWENDLKSWVFGGGTKLTVL
43586p1.2.E02.seq  QSVLTQPASASGTPGQRVTISCSGTISNIET-KYVSWY------QQLPGTAPKLLIYGNHQRPSGVPDRFSGSKSGTSASLAISGLQSEDEADYYCASWENDLKSWVFGGGTKLTVL
43586p1.2.E04.seq  QSVLTQPPSASGTPGQRVTISCSGTISNIEI-KYVSWY------QQLPGTAPKLLIYGNHQRPSGVPDRFSGSKSGTSASLAISGLQSEDEADYYCSSWENDLKSWVFGGGTKLTVL
43586p1.2.E06.seq  QSVLTQPPSASGTPGQRVTISCSGSNFNIGT-KYLYWY------QQLPGTAPKLLIYLDSQRPSGVPDRFSTSKSGTSASLAISGLQSEDEADYYCALWDDHLHGWVFGGGTKLTVL
43586p1.2.F06.seq  QSVLTQPASASGTPGQRVTISCSGTISNIET-KYVSWY------QQLPGTAPKLLIYGNHQRPSGVPDRFSGSKSGTSASLAISGLQSEDEADYYCASWENDLKSWVFGGGTKLTVL
43586p1.2.F09.seq  QSVLTQPPSASGTPGQRVTISCSGSISNIET-KYVSWY------QQLPGTAPKLLIYNSDQRPSGVPDRFSGSKSGTSASLAISGLQSEDEADYYCVSWDASLKSWVFGGGTKLTVL
43586p1.2.G04.seq  QSVLTQPLSASGTPGQRVTISCSGVSSNIEI-KYVSWY------QQLPGTAPKLLIYNSHQRPSGVPDRFSGSKSGTSASLAISGLQSEDEADYYCTSWDDRLKSWVFGGGTKLTVL
43586p1.2.G10.seq  QSVLTQPPSASGTPGQRVTISCSGSISNIET-KYVSWY------QQLPGTAPKLLIYNSDQRPSGVPDRFSGSKSGTSASLAISGLQSEDEADYYCVSWDASLKSWVFGGGTKLTVL
43586p2.A03.seq    QSVLTQPPSASGTPGQRVTISCSGSTSNIGTSRYVHWY------QQLPGTAPKLLIYFDSQRPSGVPDRFSASKSGTSASLAISGLQSEDEADYYCATWDDSLSAWVFGGGTKLTVL
43586p2.B02.seq    QSVLTQPPSASGTPGQRVTISCSGSRSNIGTNRYVHWY------QQLPGTAPKLLIYGNHQRPSGVPDRFSGSKSGTSASLAISGLQSEDEADYYCAAWDDSLSAWVFGGGTKLTVL
43586p2.B03.seq    QSVLTQPPSASGTPGQRVTISCSGGSSKIGS-KYVHWY------QQLPGTAPKLLIYKDDQRPSGVPDRFSGSKSGTSASLAISGLQSEDEADYYCAAWDDRVNAWVFGGGTKLTVL
43586p2.B05.seq    QSVLTQPPSASGTPGQRVTISCSGGSSNIGN-NFVSWY------QQLPGTAPKLLIYNEIKRPSGVPDRFSASKSGTSASLAISGLQSEDEADYYCASWDGSLRGWVFGGGTKLTVL
43586p2.C01.seq    QSVLTQPPSASGTPGQRVTISCSGGSSNIGN-NFVSWY------QQLPGTAPKLLIYNEIKRPSGVPDRFSASKSGTSASLAISGLQSEDEAOYYCASWOGSLRGWVFGGGTKLTVL
43586p2.C09.seq    QSVLTQPPSASGTPGQRVTISCSGSTSNIGTNRYVHWY------QQFPGTAPKLLIYGTDRRPSGVSDRFSGSKSGTSASLAISGLQSEDEADYYCAAWDDSLSAWVFGGGTKLTVL
```

FIG. 2

B

```
43586p2.D01.seq   QSVLTQPPSASGTPGQRVTISCSGSNSNIGA-KYLYWY------QQLPGTAPKLLIYLNDQRPSGVPDRFSGSKSGTSASLAISGLQSEDEADYYCAFWDDHLKGWVFGGGTKLTVL
43586p2.D05.seq   QSVLTQPLSASGTPGQRVTISCSGVSSNIEI-KYVSWY------QQLPGTAPKLLIYNSHQRPSGVPDRFSGSKSGTSASLAISGLQSEDEADYYCTSWDDRLKSWVFGGGTKLTVL
43586p2.D06.seq   QSVLTQPPSASGTPGQRVTISCSGVTSNIAS-YHVYWY------QQLPGTAPKLLIYLNSQRPSGVPDRFSASKSGTSASLAISGLQSEDEADYYCATWDGSLNGWVFGGGTKLTVL
43586p2.D11.seq   QSVLTQPSSASGTPGQRVAISCSGTISNIET-KYVSWYKYVSWYQQLPGTAPKLLIYNNVQRPSGVPDRFSGSQSGTSASLAISGLQSEDEAHYYCASWEGGLNSWVFGGGTKLTVL
43586p2.E08.seq   QSVLTQPLSASGTPGQRVTISCSGVSSNIEI-KYVSWY------QQLPGTAPKLLIYNSHQRPSGVPDRFSGSKSGTSASLAISGLQSEDEADYYCTSWDDRLKSWVFGGGTKLTVL
43586p2.F02.seq   QSVLTQPLSASGTPGQRVTISCSGVSSNIEI-KYVSWY------QQLPGTAPKLLIYNSHQRPSGVPDRFSGSKSGTSASLAISGLQSEDEADYYCTSWDDRLKSWVFGGGTKLTVL
43586p2.F10.seq   QSVLTQPPSASGTPGQRVTISCSASNSYIGT-KYFYWY------QQLPGTAPKLLIYLDSQRPSGVPDRFSGSKSGTSVSLAISGLQSEDEADYYCAFWDDHLHGWVFGGGTKLTVL
43586p2.F11.seq   QSVLTQPLSASGTPGQKVTISCSGVSSNIEI-KYVSWY------QQLPGTAPKLLIYNSHQRPSGVPDRFSGSKSGTSASLAISGLQSEDEADYYCTSWDDRLKSWVFGGGTKLTVL
43586p2.G01.seq   QSVLTQPPSASGTPGQRVTISCSGSNSNIGA-KYLYWY------QQLPGTAPKLLIYLNDRRPSGVPDRFSGSKSGTSASLAISGLQSEDEADYYCAFWDDHLKGWVFGGGTKLTVL
43586p2.G02.seq   QSVLTQPPSASGTPGQRVTISCSGVTSNIAS-YHVYWY------QQLPGTAPKLLIYLNSQRPSGVPDRFSASKSGTSASLAISGLQSEDEADYYCATWDGSQNGWVFGGGTKLTVL
43586p2.G10.seq   QSVLTQPSSASGTPGQRVTISCSGTISNIET-KYVSWVKYVSWYQQLPGTAPKLLIYNNVQRPSGVPDRFSGSQSGTSASLAISGLQSEDEAHYYCASWEGGLNSWVFGGGTKLTVL
43586p2.H02.seq   QSVLTQPPSASGTPGQRVTISCSASNSYIGT-KYFYWY------QQLPGTAPKLLIYLDSQRPSGVPDRFSGSKSGTSVSLAISGLQSEDEADYYCAFWDDHLHGWVFGGGTKLTVL
43645p1.B02.seq   QSGLTQPPSASGTPGQRVTISCSGDISNTRN-NYVSWY------QQLPGTAPKLLIYGNHQRPSGVPDRFSGSKSATSASLAISGLQSEDEADYHCGTWDNTLNAWVFGGGTKLTVL
43645p1.B08.seq   QSVLTQPPSASGTPGQRVTISCSGSNSNIRN-NFVSWY------QHLPGMAPKLLIYGNSQRPSGVPDRFSGSKSGTSASLAISGLQSEDEADYYCTSWDFSVNGWVFGGGTKLTVL
43645p1.C09.seq   QSVLTQPPSASGTPGQRVTISCSGSNSNIRN-NFVSWY------QHLPGTAPKLLIYGNSQRPSGVPDRFSGSKSGTSASLAISGLQSEDEADYYCTSWDFSVSGWVFGGGTKLTVL
43645p1.C11.seq   QSGLTQPPSASGTPGQRVTISCSGDISNTRN-NYVSWY------QQLPGTAPKLLIYGNHQRPSGVPDRFSGSKSATSASLAISGLQSEDEADYYCGTWDNTLNAWVFGGGTKLTVL
43645p1.D01.seq   QSVLTQPPSASGTPGQRVIISCSGTNSNIGS-NHVNWY------QQLPGTAPKLLIYTNNQRPSGVPDRFSGSASGTSASLAISGVQSEDEADYYCAAWDGSLNGWVFGGGTKLTVL
43645p1.D03.seq   QSGLTQPPSASGTPGQRVTISCSGDISNTRN-NYVSWY------QQLPGTAPKLLIYGNHQRPSGVPDRFSGSKSATSASLAISGLQSEDEADYYCGTWDNTLNAWVFGGGTKLTVL
43645p1.D07.seq   QSVLTQPPSASGTPGQRVTISCSGSTSNVGD-HYVHWY------QQLPGTAPKLLIYKDDQRPSGVPDRFSGSKSGTSASLAISGLQSEDEADYYCSTWDNTLNGWVFGGGTKLTVL
43645p1.D08.seq   QSVLTQPPSASGTPGQRVIISCSGTNSNIGS-NHVNWY------QQLPGTAPKLLIYTNNQRPSGVPDRFSGSASGTSASLAISGVQSEDEADYYCAAWDGSLNGWVFGGGTKLTVL
43645p1.E03.seq   QSVLTQPPSASGTPGQRVTISCSGVTSNIRN-SYVSWY------QQLPGTAPKLLIYGNDQRPSGVPDRFSGSKSGTSASLAISGLQSEDEADYYCGTWDNTLNAWVFGGGTKLTVL
43645p1.F07.seq   QSVLTQPPSASGTPGQRVTISCSGSNSNIRN-NFVSWY------QHLPGTAPKLLIYGNSQRPSGVPDRFSGSKSGTSASLAISGLQSEDEADYYCTSWDFSVNGWVFGGGTKLTVL
43645p1.F11.seq   QSGLTQPPSASGTPGQRVTISCSGDISNTRN-NYVSWY------QQLPGTAPKLLIYRNSQRPSGVPDRFSGSKSATSASLAISGLQSEDEADYYCGTWDNTLNAWVFGGGTKLTVL
43645p1.F12.seq   QSVLTQPPSASGTPGQRVTISCSGSSSNIQS-NYVYWY------QQLPGTAPKLLIYGNHQRPSGVPDRFSGSKSDTSASLAISGLQSEDEADYYCATWDASLNVWVFGGGTKLTVL
43645p1.G05.seq   QSVLTQPPSASGTPGQRVTISCSGVTSNIRN-YYVSWY------QQLPGTAPKLLIYGNDQRPSGVPDRFSGSKSGTSASLAISGLQSEDEADYYCGTWDNTLNAWVFGGGTKLTVL
43645p1.H10.seq   QSVLTQPPSVSGTPGQRVTISCSGTISNVGN-KYVSWY------QQVPGTAPKLLIDYN-QRPSGVPDRFSGSQSGTSASLTISGLQSEDEADYYCATWDDSLKGWVFGGGTKLTVL
```

LC CDR1 LC CDR2 LC CDR3

FIG. 2 (Cont.)

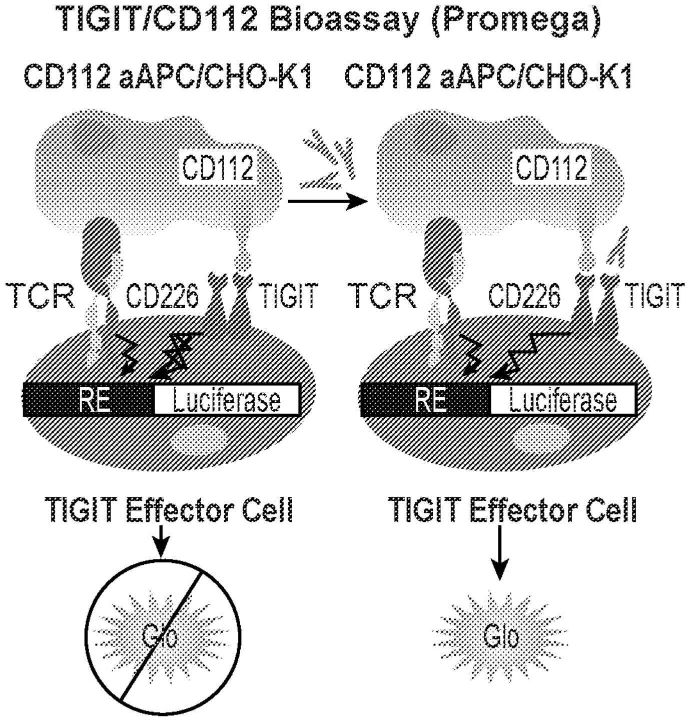
- Assay cells: TIGIT Effector Cells (Jurkat T cells)
  CD112 aAPC/CHO-K1 cells
- Medium: RPMI 1640 + FBS
- Test antibodies: Omnichicken anti-TIGIT antibodies 0.3, 3 μg/mL
- Incubation time: 16 hr
- Detection reagents: Bio-Glo Luciferase assay substrate/buffer
- Luminescence reader: Glomax navigator
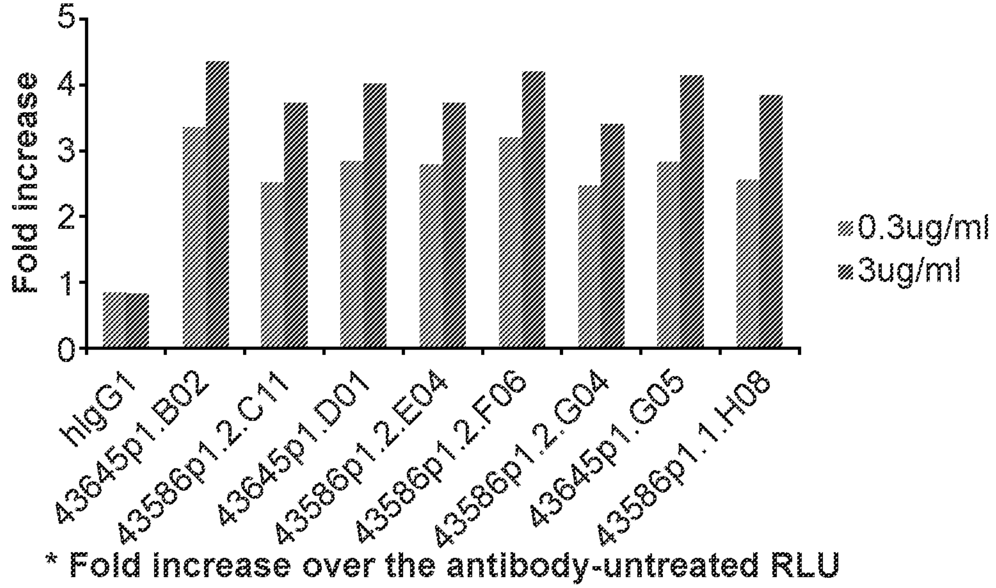
* Fold increase over the antibody-untreated RLU
FIG. 5

| Antibody # | Platform | SPR (KD, M) | Cross-reactivity1) | SEC HPLC (%) | TIGIT/CD155 bioassay (fold increase)2) | TIGIT/CD122 bioassay (fold increase)2) |
|---|---|---|---|---|---|---|
| 43645p1.B02 | OmniChicken | 4.6E-11 | H,C,M | 94.4 | 3.3 | 3.3 |
| 43586p1.2.C11 | OmniChicken | 5.2E-11 | H,C,M | 94.4 | 3.5 | 2.5 |
| 43645p1.D01 | OmniChicken | 3.4E-10 | H,C | - | 4.1 | 2.8 |
| 43586p1.2.E04 | OmniChicken | 1.2E-10 | H,C,M | 90.6 | 3.8 | 2.8 |
| 43586p1.2.F06 | OmniChicken | 2.2E-10 | H,C,M | 95.9 | 3.6 | 3.2 |
| 43586p1.2.G04 | OmniChicken | 3.9E-11 | H,C,M | 90.2 | 3.2 | 2.5 |
| 43645p1.G05 | OmniChicken | 5.1E-11 | H,C,M | 95.6 | 3.8 | 2.8 |
| 43586p1.1.H08 | OmniChicken | 2.9E-10 | H,C | 91.0 | 3.1 | 2.5 |

1) H, human; C, cynomolgus monkey; M, mouse

2) Fold increase of antibody conc 0.3ug/ml

FIG. 6

ANTI-TIGIT ANTIBODY AND METHODS OF USE THEREOF

CROSS-REFERENCING

This application is a § 371 national phase of International Application No. PCT/US2021/039664, filed on Jun. 29, 2021, which claims the benefit of U.S. provisional application Ser. No. 63/061,533, filed on Aug. 5, 2020, which applications are incorporated by reference herein.

BACKGROUND

TIGIT (T-cell immunoreceptor with Ig and ITIM domains), also known as WUCAM, Vstm3 or Vsig9, is a co-inhibitory receptor protein that limits T cell proliferation and activation. The protein is expressed on subsets of T cells, particularly activated, memory, and regulatory T cells as well as natural killer (NK) cells. It is thought that TIGIT mediates its immunosuppressive effect by competing with CD226 (also known as DNAM-1) for binding to the same set of ligands: CD155 (also known as PVR) and CD112 (also known as PVRL2) (see, e.g., Levin et al Eur. J. Immunol., 2011, 41: 902-915). It is thought that CD155 binds with a higher affinity to TIGIT than to CD226 and thus when TIGIT is present CD226 signaling is inhibited and T cell proliferation and activation are limited.

TIGIT is upregulated on tumor antigen-specific $CD8^+$ T cells and $CD8^+$ tumor-infiltrating lymphocytes (TILs). Blockade of TIGIT by cells that express a TIGIT ligand (CD155) increased the proliferation, cytokine production, and degranulation of both of these cells (Chauvin et al., J Clin Invest., 2015 125: 2046-2058). TIGIT may also play a role in evasion of immunosurveillance by tumor cells. For example, CD155 is over-expressed on melanoma cells (Inozume et al J. Invest. Dermatol. 2014 134 S121) and various other tumors and the TIGIT/CD155 interaction shields those tumor cells from immune-mediated eradication by inhibiting anti-tumor responses of T and NK cells (see, e.g., Stanietsky et al Proc. Nat'l Acad. Sci. 2009 106: 17858 and Lozano et al J. Immunol. 2012 188: 3869).

It is thought that TIGIT may downregulate immune responses similarly to other co-inhibitory receptors such as CTLA-4, PD-1 and BTLA. Thus, TIGIT represents a potential therapeutic target for stimulating anti-tumor T cell responses in patients. In particular, in mouse models, blockade of both PD-L1 and TIGIT using antibodies against those proteins leads to a synergistic enhancement of $CD8^+$ T cell mediated tumor rejection (see, Grogan et al. J. Immunol. 2014 192: 15 and Johnston et al. Cancer Cell 2014 26:1-15). Similar results have been obtained in animal models of melanoma (see, e.g., Inozume et al. J. Invest. Dermatol. 2014 134:S121), and some experiments suggest that TIGIT blockade is effective to enhance anti-tumor $CD8^+$ T cell response only in the presence of the co-activating receptor CD226, which competes with TIGIT for binding to CD155 (Johnston et al. Cancer Cell 2014 26:1-15).

As such, there is currently a need for antibodies that block TIGIT. Such antibodies can be used to treat various malignancies, particularly when combined with another immune checkpoint inhibitor such as a PD-1/PD-L1 inhibitor.

SUMMARY OF THE INVENTION

The present disclosure provides antibodies that specifically bind to and some embodiments inhibit TIGIT. The antibodies are useful in various treatment, diagnostic, and monitoring applications, which are also provided.

In some embodiments, the antibody may comprise: (a) a variable domain comprising: i. heavy chain CDR1, CDR2 and CDR3 regions that are identical to the heavy chain CDR1, CDR2 and CDR3 regions of an antibody selected from FIG. 1; and ii. light chain CDR1, CDR2 and CDR3 regions that are identical to the light chain CDR1, CDR2 and CDR3 regions of an antibody selected from FIG. 2; or (b) a variant of said variable domain of (a) that is otherwise identical to said antibody variable domain except for up to 10 (e.g., up to 9, 8, 7, 6, 5, 4, 3, 2, or 1) amino acid substitutions in the collective CDR regions of the variable domain of (a).

In some embodiments, the antibody comprises: a heavy chain variable domain comprising an amino acid sequence that is at least 90% (e.g., at least 95%) identical to the amino acid sequence of the heavy chain variable domain of an antibody selected from FIG. 1; and a light chain variable domain comprising an amino acid sequence that is at least 90% (e.g., at least 95%) identical to the light chain variable domain of the antibody, selected from FIG. 2.

The antibodies whose variable domain sequences are shown in FIGS. 1 and 2 are essentially "human" antibodies made by chickens and, as such, can bind to epitopes in TIGIT that are in a variety of mammals, such as humans, mice and monkeys. Those epitopes should not be immunogenic in mammals (since they are already present) and, as such, the present antibodies are believed to bind to some new epitopes. Moreover, because the present antibodies can bind to TIGIT from multiple mammals, the present antibodies may be advantageous because their therapeutic potential can be readily tested in mammalian model systems for cancer (e.g., mice).

BRIEF DESCRIPTION OF THE DRAWINGS

FIG. 2 panels A and B provide the amino acid sequence of 54 anti-TIGIT antibody light chain variable regions, in which the complementarity determining regions (CDRs) as defined by the Chothia method are indicated by boxes. From top to bottom: SEQ ID NOS: 55-108.

FIG. 5 shows the results of a TIGIT/CD122 bioassay on 8 selected antibodies.

FIG. 6 is a table summarizing some of the results obtained for 8 selected antibodies.

DEFINITIONS

Figure 1:
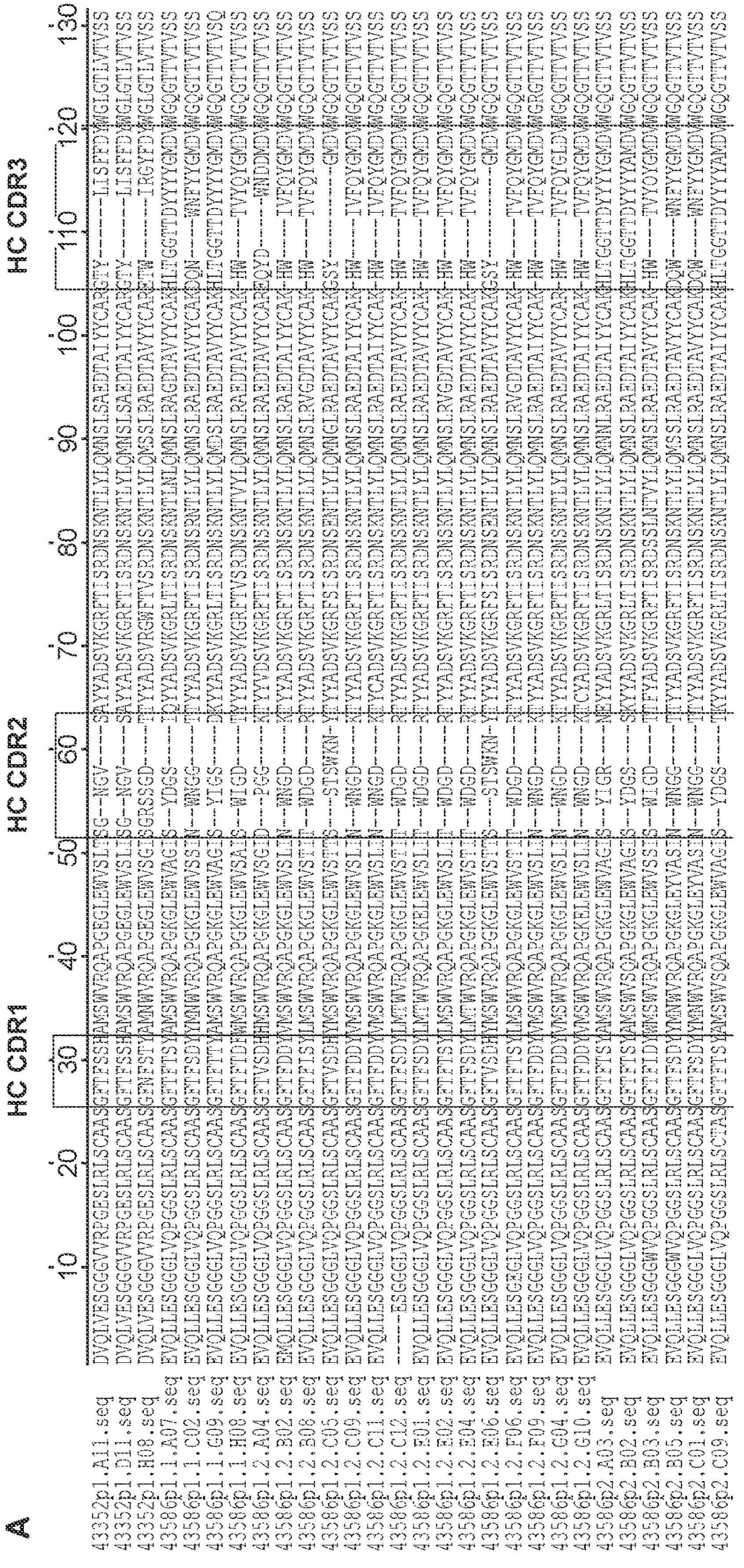
FIG. 1 panels A and B provide the amino acid sequence of 54 anti-TIGIT antibody heavy chain variable regions, in which the complementarity determining regions (CDRs) as defined by the Chothia method are indicated by boxes. From top to bottom: SEQ ID NOS: 1-54.
Figure 1:
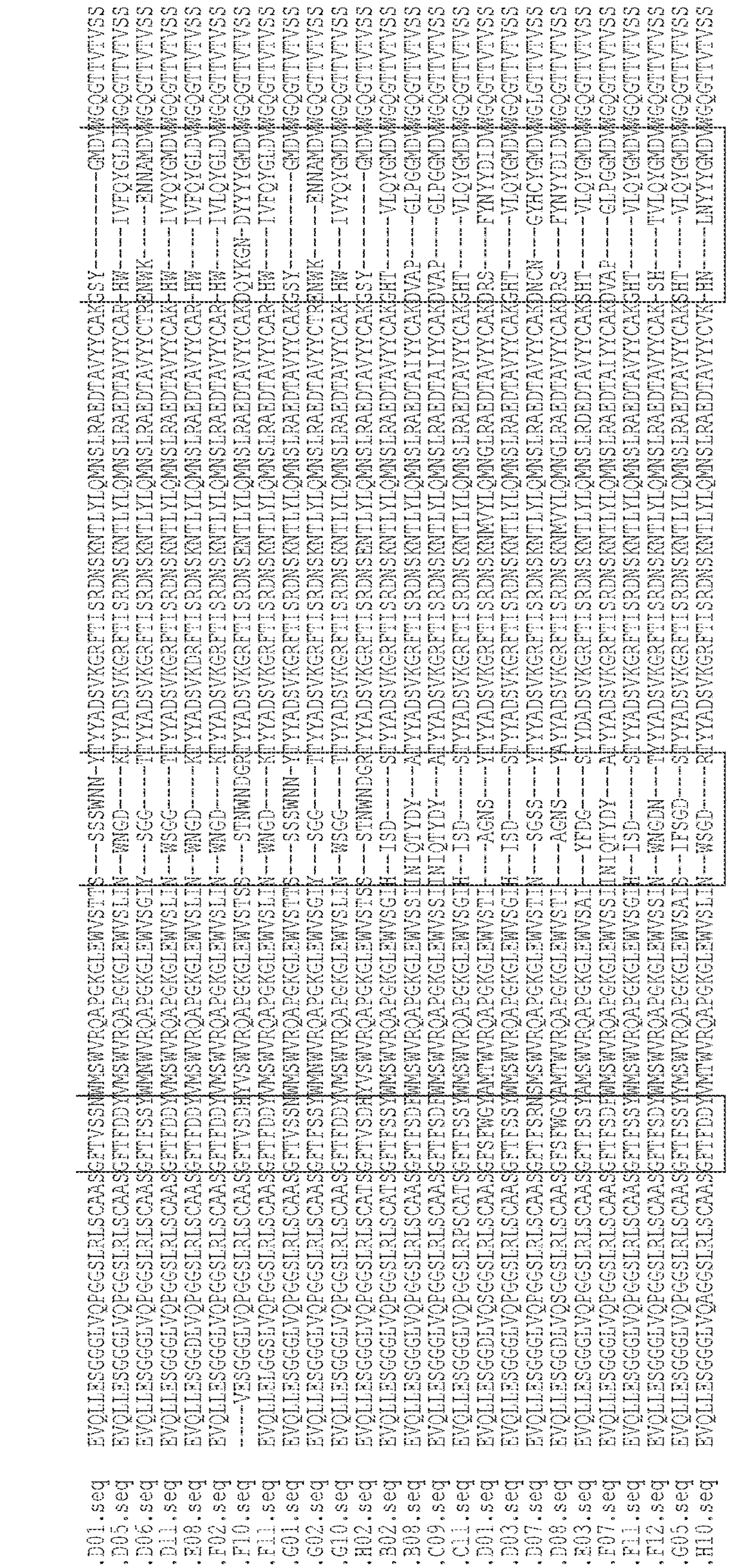
Figure 3:
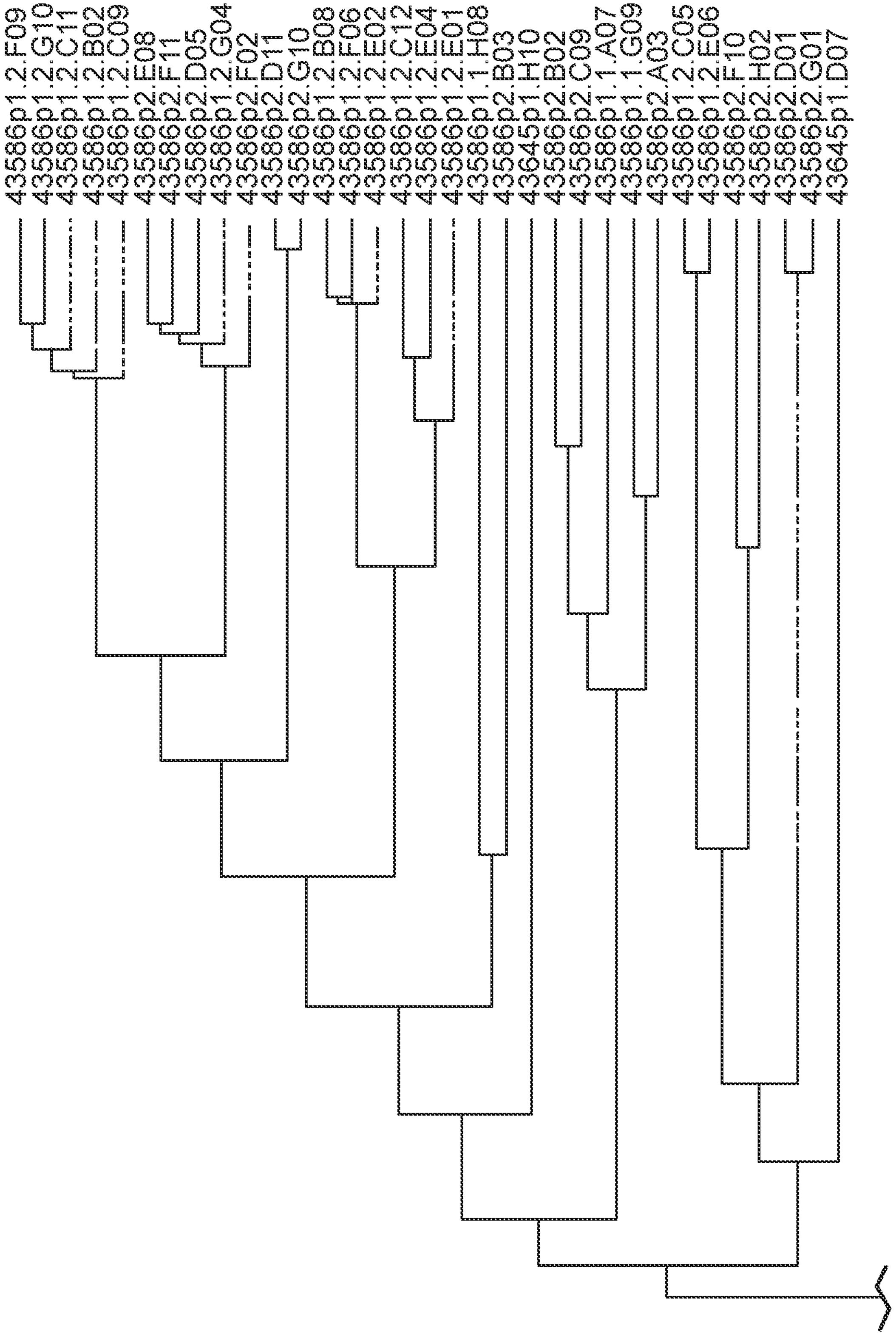
FIG. 3 is a dendrogram showing the phylogenetic relationship of the 54 anti-TIGIT antibodies based on sequence comparisons (amino acid substitutions per 100 residues). Analysis of the dendrogram yields lineage groups. Each lineage group has less than 10 amino acid substitutions for 100 residues. The antibodies in each lineage group may have descended from a common ancestor via affinity maturation. Consensus sequences for the CDRs in each lineage group can be readily derived.
Figure 3:
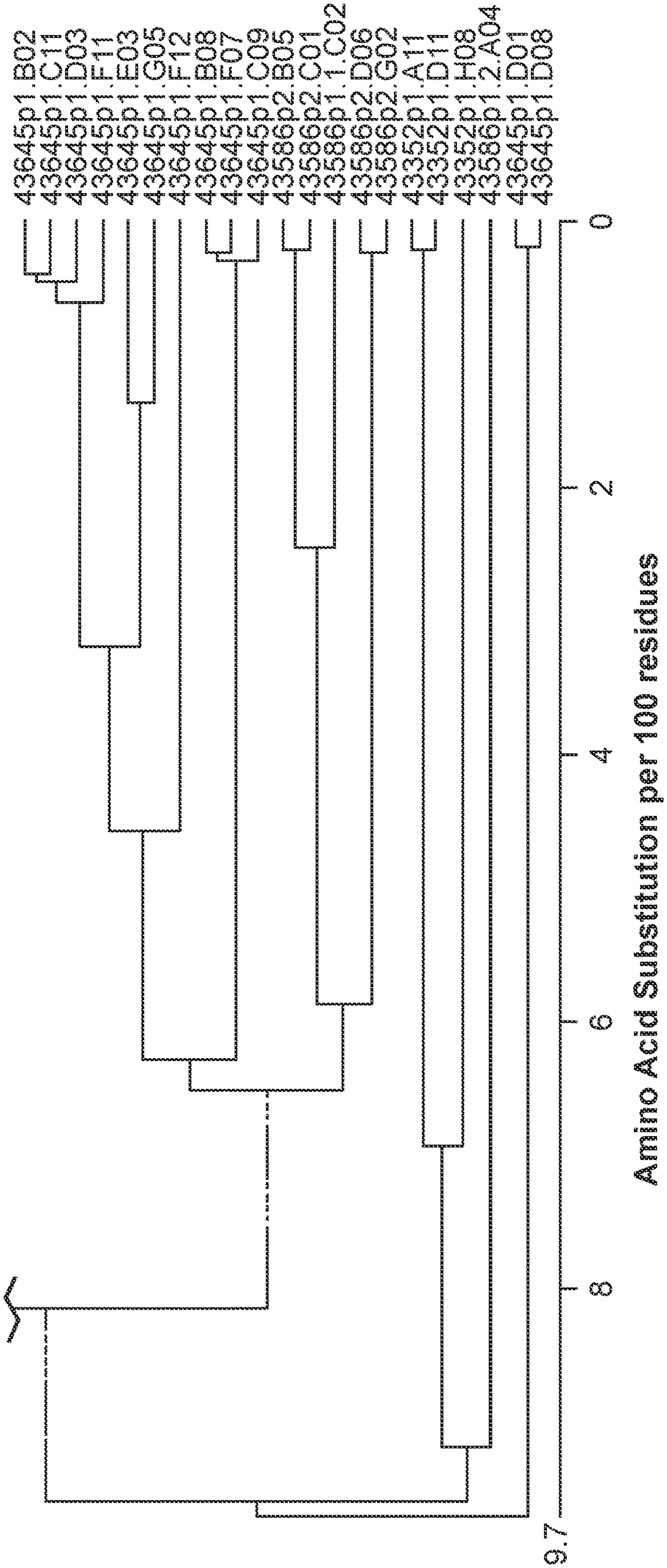

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies, vol.* 113, *Rosenburg and Moore eds., Springer-Verlag, New York, pp.* 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An anti-TIGIT antibody binds specifically to an epitope within a TIGIT polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The CDRs indicated in FIGS. 1 and 2 are defined by the Chothia method. However, as indicated below, the Kabat and MacCallum method could also be used to define the CDRs.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term “framework” when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term “framework region” is intended to mean each domain of the framework that is separated by the CDRs.

An “isolated” antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody’s natural environment will not be present. In some instances, isolated antibody will be prepared by at least one purification step.

As used herein, the terms “treatment,” “treating,” and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. “Treatment,” as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms “individual,” “subject,” “host,” and “patient,” used interchangeably herein, refer to a mammal, including, but not limited to, murines (rats, mice), non-human primates, humans, canines, felines, ungulates (e.g., equines, bovines, ovines, porcines, caprines), etc.

A “therapeutically effective amount” or “efficacious amount” refers to the amount of an anti-TIGIT antibody that, when administered to a mammal or other subject for treating a disease, is sufficient to effect such treatment for the disease. The “therapeutically effective amount” will vary depending on the anti-TIGIT antibody, the disease and its severity and the age, weight, etc., of the subject to be treated.

A “biological sample” encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term “biological sample” encompasses a clinical sample, and also includes cells in culture, cell supernatants, cell lysates, serum, plasma, biological fluid, and tissue samples.

As used herein, the term “collectively” in the context of a variant of an antibody variable domain that is otherwise identical to the antibody variable domain except for a defined number of amino acid substitutions “in the collective CDR regions of the antibody variable domain”, indicates that the number of amino acid substitutions is counted using all six CDRs. Explained by example, if the variant has 5 amino acid substitutions relative to the antibody variable domain, then the six CDRs of the variant, combined, have a total of 5 amino acid substitutions relative to the antibody variable domain. This phrase is not intended to mean that each CDR has a defined number of amino acid substitutions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a,” “an,” and “the” include plural referents unless the context clearly dictates otherwise. Thus, for example, reference to “an antibody” includes a plurality of such antibodies and reference to “the anti-TIGIT antibody” includes reference to one or more anti-TIGIT antibodies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibodies specific for human TIGIT. The antibodies are useful in various treatment, diagnostic, and monitoring applications, which are also provided.

Antibodies

A subject antibody specifically binds TIGIT from humans and other mammals, e.g., monkey and mouse.

A subject antibody may have high affinity binding to TIGIT from humans and other mammals, e.g., monkey and mouse. For example, a subject antibody may bind to human, monkey and/or mouse TIGIT with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to an epitope present on human, monkey and/or mouse TIGIT with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject antibody can in some embodiments reduce binding of TIGIT to a TIGIT ligand and/or reduce the activity of TIGIT signaling. For example, in some embodiments a subject antibody can reduce binding of TIGIT to a TIGIT ligand or reduce TIGIT signaling by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of binding between TIGIT and the TIGIT ligand or TIGIT signalling in the absence of the antibody. In some embodiments, the antibody may be conjugated to a cytotoxic moiety such that cells producing TIGIT are killed.

The term "antibody" refers to a protein comprising one or more (e.g., one or two) heavy chain variable regions ($V_H$) and/or one or more (e.g., one or two) light chain variable regions ($V_L$), or subfragments thereof capable of binding an epitope. The $V_H$ and $V_L$ regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4 Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulfide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, a subject antibody is an IgG isotype.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and/or a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to TIGIT as described above. Examples of binding fragments include (i) a Fab fragment (a monovalent fragment consisting of the VL, VH, CL and CH1 domains; (ii) a $F(ab')_2$ fragment (a bivalent fragment comprising two Fab fragments linked by a disulfide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, a subject antibody comprises: a variable domain comprising: a) a heavy chain variable domain comprising: i. a CDR1 region that is identical in amino acid sequence to the sequence of a heavy chain CDR1 region of an antibody selected from the antibodies shown in FIGS. 1 and 2; ii. a CDR2 region that is identical in amino acid sequence to the sequence of a heavy chain CDR2 region of the selected antibody; and iii. a CDR3 region that is identical in amino acid sequence to the sequence of a heavy chain CDR3 region of the selected antibody; and b) a light chain variable domain comprising: i. a CDR1 region that is identical in amino acid sequence to the sequence of a light chain CDR1 region of the selected antibody; ii. a CDR2 region that is identical in amino acid sequence to that of alight chain CDR2 region of the selected antibody sequence; and iii. a CDR3 region that is identical in amino acid sequence to that of a light chain CDR3 region of the selected antibody; wherein the antibody specifically binds human, monkey, rat and/or mouse TIGIT.

In certain embodiments, an antibody comprising: (a) a variable domain comprising: i. a CDR1 region that is identical in amino acid sequence to the heavy chain CDR1 region of an antibody selected from the antibodies shown in FIGS. 1 and 2; ii. a CDR2 region that is identical in amino acid sequence to the heavy chain CDR2 region of the selected antibody; and iii. a CDR3 region that is identical in amino acid sequence to the heavy chain CDR3 region of the selected antibody; and a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; or (b) a variant of the variable domain of part (a) that is otherwise identical to the variable domain of part (a) except for up to 10 (e.g., up to 9, 8, 7, 6, 5, 4, 3, 2, or 1) amino acid substitutions in the collective CDR regions of the variable domain of (a), wherein the antibody binds to TIGIT.

In some embodiments, the antibody may contain only a heavy chain variable domain described herein. In these embodiments, the antibody may be a "heavy chain only" antibody.

The heavy and light chain sequences disclosed herein can be analyzed via lineage analysis in order obtain consensus sequences for the CDRs. Groups of sequences that are believed to be related by lineage are indicated in FIGS. 1 and 2. Analysis of these sequences reveals which amino acid positions can tolerate amino acid substitutions and, as such, can be used to make variants of the present antibodies that have, for example, amino acid substitutions in the CDRs.

In some embodiments, a subject antibody (e.g., a subject antibody that specifically binds TIGIT may) comprise: a) a light chain region comprising: i) one, two, or three complementarity determining regions (CDRs) from a light chain variable region sequence of a selected anti-TIGIT antibody; and ii) a light chain framework region, e.g., a framework region from a human immunoglobulin light chain; and b) a heavy chain region comprising: i) one, two, or three CDRs from the heavy chain variable region sequence of a selected antibody; and ii) a heavy chain framework region, e.g., a framework region from a human immunoglobulin heavy chain.

A subject antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to a sequence depicted in FIG. 1 which are set forth in SEQ ID NOS:1-54. A subject antibody can comprise a heavy chain variable region comprising one, two, or three of the heavy chain complementarity determining regions (CDRs) of a selected anti-TIGIT antibody.

A subject antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 2 which are set forth in SEQ ID NOS:55-108. A subject antibody can comprise a light chain variable region comprising one, two, or three of the light chain CDRs of a selected anti-TIGIT antibody.

In some embodiments, a subject antibody comprises anti-TIGIT antibody heavy chain CDRs and anti-TIGIT antibody light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; an light chain CDR1 of a selected anti-TIGIT antibody; a second amino acid sequence of from about 5 amino acids to about 25 amino acids in length; a light chain CDR2 of a selected anti-TIGIT antibody; a third amino acid sequence of from about 5 amino acids to about 25 amino acids in length; a light chain CDR3 of a selected anti-TIGIT antibody; a fourth amino acid sequence of from about 5 amino acids to about 25 amino acids in length; a heavy chain CDR1 of a selected anti-TIGIT antibody; a fifth amino acid sequence of from about 5 amino acids to about 25 amino acids in length; a heavy chain CDR2 of a selected anti-TIGIT antibody; a sixth amino acid sequence of from about 5 amino acids to about 25 amino acids in length; a heavy chain CDR3 of a selected anti-TIGIT antibody; and a seventh amino acid sequence of from about 5 amino acids to about 25 amino acids in length.

In some embodiments, a subject antibody may comprise, in order from N-terminus to C-terminus: a light chain FR1 region; a light chain CDR1 of a selected anti-TIGIT antibody; a light chain FR2 region; a light chain CDR2 of a selected anti-TIGIT antibody; a light chain FR3 region; a light chain CDR3 of a selected anti-TIGIT antibody; optionally a light chain FR4 region; a linker region; optionally a heavy chain FR1 region; a heavy chain CDR1 of a selected anti-TIGIT antibody; a heavy chain FR2 region; a heavy chain CDR2 of a selected anti-TIGIT antibody; a heavy chain FR3 region; a heavy chain CDR3 of a selected anti-TIGIT antibody; and a heavy chain FR4 region. In some of these embodiments, each of the FR regions is a human FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers, glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). There are several examples of flexible linkers known in the art. The ordinarily skilled artisan will recognize that design of a peptide conjugated to any elements described above can include linkers that are all or partially flexible, such that the linker can include a flexible linker as well as one or more portions that confer less flexible structure.

The antibodies shown in FIGS. 1 and 2 are already human since they are largely composed of human germline sequence. In some embodiments, a subject antibody is "humanized" The term "humanized antibody" refers to an antibody comprising at least one chain comprising variable region framework residues substantially from a human antibody chain (referred to as the acceptor immunoglobulin or antibody) and at least one CDR substantially from a mouse antibody, (referred to as the donor immunoglobulin or antibody). See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. In some embodiments, a subject antibody comprises one or more of the CDRs and one or more FR regions from a human antibody. Methods of making humanized antibodies are known in the art. See, e.g., U.S. Pat. No. 7,256,273.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to an the subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate;

cellulose acetate butyrate; cellophane; cellulose nitrate; cellulose propionate; cellulose ethers; amorphous Teflon; poly (ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O—CH_2—CH_2)_nO—R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{1231}I$ (iodine), $^{18}F$ (fluorine), $^{99}Tc$ (technetium), $^{111}In$ (indium), and $^{67}Ga$ (gallium), and contrast agent such as gadolinium (Gd), dysprosium, and iron. Radioactive Gd isotopes ($^{153}Gd$) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., $(His)_n$, e.g., 6His, and the like; provide for secretion of the fusion protein from a cell; provide an epitope tag, e.g., GST, hemagglutinin (HA) FLAG, c-myc, and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5, HisX6, C-myc, Flag, StrepTag, hemagglutinin, glutathinone-S-transferase (GST), thioredoxin, cellulose binding domain, chitin binding domain, S-peptide, T7 peptide, SH2 domain, C-end RNA tag, metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_XH_YN_Z$, can be cyclic or acyclic, branched or unbranched, hydrocarbon chains of 3-12 carbon atoms that further include 1-6 NR or $N(R)_2$ moieties, wherein R is H, ($C_1$-$C_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Methods of Producing a Subject Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy- and light-chain CDRs. In some embodiments, a subject nucleic acid comprises a nucleotide sequence encoding heavy- and light-chain CDRs, where the CDR-encoding sequences are interspersed with FR-encoding nucleotide sequences. In some embodiments, the FR-encoding nucleotide sequences are human FR-encoding nucleotide sequences.

Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli.*

Formulations and Pharmaceutical Compositions

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in tumor size or amelioration of a symptom. Generally, the desired result is at least a reduction in a symptom of cancer as compared to a control. A subject antibody can be delivered in such a manner as to avoid the blood-brain barrier, as described in more detail below. A subject antibody can be formulated and/or modified to enable the antibody to cross the blood-brain barrier, if necessary. A treatment involves administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with the subject invention. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, Novel Drug Delivery Systems, 1992 (Marcel Dekker, Inc.). Some of these formulations are discussed herein.

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

In some embodiments, the antibody can be administered to the patient as an intravenous infusion (200 mg or 2 mg/kg, up to 200 mg) over 10-60 (e.g., 30 minutes), every 2-4 (e.g., three) weeks in a pharmaceutically acceptable carrier, e.g., PBS.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Treatment Methods

The present disclosure provides methods of treating a cancer, the methods generally involving administering to an individual in need thereof (e.g., an individual having cancer) an effective amount of a subject antibody, alone (e.g., in monotherapy) or in combination (e.g., in combination therapy) with one or more additional therapeutic agents.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of cancer by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

In some embodiments, an effective amount of a subject antibody is an amount that, when administered alone (e.g., in monotherapy) or in combination (e.g., in combination therapy) with one or more additional therapeutic agents, in one or more doses, is effective to decrease tumor size in the individual being treated. For example, an effective amount of a subject antibody can decrease tumor size in an individual by at least about 5%, at least about 10%, at least about 15%, at least about 20%, at least about 25%, at least about 30%, at least about 40%, at least about 50%, or more, compared to tumor size in the absence of treatment with the antibody.

Combination Therapy

In some embodiments, a subject treatment method involves administering a subject antibody and one or more additional therapeutic agents. Suitable additional therapeutic agents include, but are not limited to an immune checkpoint inhibitor such as an an anti-CTLA-4 antibody, anti-PD1 antibody, an anti-PD-L1 antibody, an anti-TIM-3 antibody, an anti-VISTA antibody, an anti-LAG-3 antibody, an anti-IDO antibody, or an anti-MR antibody, although others are known. In some embodiments, the treatment may also include a co-stimulatory antibody such as an antibody against CD40, GITR, OX40, CD137, or ICOS, for example. In some embodiments, the antibody may be an anti-PD-1 antibody, an anti-PD-L1 antibody or an anti-CTLA-4 antibody. Examples of such antibodies include, but are not limited to: Ipilimumab (CTLA-4), Nivolumab (PD-1), Pembrolizumab (PD-1), Atezolizumab (PD-L1), Avelumab (PD-L1), and Durvalumab (PD-L1). These therapies may be combined with one another and/or with other therapies. In some embodiments, the dose administered may be in the range of 1 mg/kg to 10 mg/kg, or in the range of 50 mg to 1.5 g every few weeks (e.g., every 3 weeks), depending on the weight of the patient. In certain embodiments, the patient will be treated with the antibody or antibodies without knowing the PD1, PD-L1, CTLA-4, TIM-3, VISTA, LAG-3, IDO or KIR status of the tumor.

Subjects Suitable for Treatment

A variety of subjects are suitable for treatment with a subject method. Suitable subjects include any individual, e.g., a human, who has cancer, who has been diagnosed with cancer, who is at risk for developing cancer, who has had cancer and is at risk for recurrence of cancer, or who is recovering from cancer. In some embodiments, the patient may have a hematopoietic cell cancer such as multiple myeloma (see, e.g., van de Donk Front Immunol. 2018; 9: 2134). In these embodiments, the TIGIT antibody may have Fc-dependent immune effector mechanisms, such as complement-dependent cytotoxicity (CDC), antibody-dependent cellular cytotoxicity (ADCC), and antibody-dependent cellular phagocytosis (ADCP). Inhibition of ectoenzymatic function and direct apoptosis induction may also contribute to the efficacy of these antibodies to kill multiple myeloma cells.

In other embodiments, the antibody may be used as an immune checkpoint inhibitor in possible combination with another immune checkpoint inhibitor to treat patients that have, e.g., melanoma of the skin, non-small cell lung cancer, kidney cancer, bladder cancer, head and neck cancers, and Hodgkin lymphoma, all of which can be treated by immune blockade. Anti-TIG antibodies are also useful for the treatment of several cancers, including nonsmall cell lung cancer, colorectal carcinoma, melanoma, acute myeloid leukaemia, for example.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation and Characterization of Anti-TIGIT Antagonist Antibodies

Anti-TIGIT human monoclonal antibodies were generated using transgenic chickens (OMNICHICKEN™) that express human antibody genes: human light chain (VLCL or VKCK) and human VH while expressing the chicken constant regions of the heavy chain (Ching et al 2018 MAbs. 2018 10: 71-80).

Three transgenic chickens were immunized initially with 100 ug of Fc-tagged human TIGIT (Acro Biosystems #TIT-H5254), boosted 14 days later with 100 ug of Fc-tagged murine TIGIT (Acro Biosystems #TIT-M5257), boosted 14 days later with 100 ug of Fc-tagged human TIGIT, and 14 days later with 100 ug Fc-tagged murine TIGIT. A final boost of 60 ug of each human and murine Fc-tagged TIGIT was administered IV 4 days before harvesting the spleen. The serum immune response was monitored by ELISA on human and murine his-tagged TIGIT (Acro Biosystems #TIT-H52H3 and #TIT-M52E6, respectively).

Splenocytes were isolated and tested using the GEM assay as described (Mettler Izquierdo et al 2016). Briefly, large beads (Life Technologies #A37306) were coated with human his-tagged TIGIT and smaller beads (Life Technologies #A37296) were coated with mouse his-tagged TIGIT overnight. Beads were blocked in 3% milk in DPBS for 1 h at room temperature then washed three times in DPBS. Beads were mixed in the ratio 5:1 (small over large beads) with 1e7 primary splenocytes and an Alexa Fluor 594-conjugated goat anti-chicken IgY (Thermo Fisher Scientific #A-11042) for the detection. The mixture was plated and positive clones were detected under microscope using a CY3 filter. Cells secreting IgY that bound to the beads were selected.

Antibody cloning and binding confirmation: Positive clones were transferred into a 96-well plate containing a PCR mixture consisting of dNTP, primers and enzyme mix. The variable regions of heavy and light chains were cloned and assembled into a single chain Fv-Fc mammalian expression vector. Sanger sequencing was performed by GeneWiz and sequences were evaluated using DNASTAR Lasergene 15. Unique scFv-Fcs were transiently expressed in Expi293 cells (Life Technologies, #A14527) grown in Expi293 Expression Medium (Life Technologies, #A1435101) after transfection using ExpiFectamine 293 transfection reagent and supplements (Life Technologies, #A14524). Cells were incubated for 3-5 days with shaking at 37° C. in a 5% CO2 humidified incubator. Supernatants were harvested, quantitated using a Blitz Instrument (Pall ForteBio), and tested for binding activity by ELISA on plates coated with His-tagged-TIGIT proteins of different species (human, mouse, and cynomolgus monkey [Acro Biosystems #TIT-05223]), rabbit anti-huFc (positive control; Rockland #609-4103) or an irrelevant his-tagged protein (negative control). All but 3 antibodies showed significant binding to cyno TIGIT by Elisa, and 36 bound murine TIGIT by Elisa.

Binding of anti-TIGIT antibodies to cells expressing human TIGIT was assessed by flow cytometry. Briefly, approximately 1.5e5 TIGIT/NFAT reporter Jurkat cells (BPS Bioscience #60538)) or parental NFAT reporter Jurkat cells (BPS Bioscience #60621) were resuspended in FACS buffer (PBS/10% BSA/0.01% NaN3) containing 10 ug/ml of anti-TIGIT antibodies and incubated for 60 min on ice. Cells were washed twice and resuspended in FACS buffer containing AlexaFluor 647-conjugated donkey anti-human Fc (Jackson ImmunoResearch Laboratories #709-605-098) for 60 min on ice. Cells were then washed twice, resuspended in FACS buffer, and read on an Attune Flow Cytometer (Life Technologies). Data are expressed as Mean Fluorescent Intensities (MFI). A total of 54 antibodies showed significant binding to cells expressing human TIGIT.

Binding affinities of anti-TIGIT antibodies to human, cyno, and murine TIGIT were measured by Surface Plasmon Resonance (SPR) on a Carterra LSA instrument. Goat anti-human Fc antibody was amine coupled to a HC30M chip. ScFv-Fc supernatants were diluted 30-fold with HBSTE and were captured by the anti-human Fc coupled HC30M chip. A 1:2 dilution series of his-tagged human TIGIT, starting at 400 nM, was injected onto the chip for binding. A dilution series was also carried out for cyno TIGIT and murine TIGIT. Data were analyzed using the Carterra™ Kinetics software.

Epitope Binning: Supernatants containing scFv-Fcs (referred to as ligand scFv-Fcs) were diluted 50-fold and coupled to a HC2000M chip via sulpho-NHS/EDC coupling chemistry, then blocked with ethanolamine. In each cycle of the binning experiment, 100 nM his-tagged-human TIGIT was injected to the whole array, and then an individual supernatant scFv-Fc (referred to as an analyte scFv-Fc), diluted 40-fold in HBSTE+BSA, was injected to the whole array to sandwich the antigen bound to the ligand scFv-Fc. At the end of each cycle the chip was regenerated with 10 mM Glycine pH 2 to remove bound antigen and analyte scFv-Fc. This procedure was repeated for all analyte supernatants. Epitope binning analysis was performed with the Carterra epitope software. Two epitope bins were identified in this antibody cohort.

TIGIT/CD155 Blockade Assay: The ability of anti-TIGIT antibodies to block TIGIT/CD155 interaction was determined using the Promega TIGIT/CD155 Blockade Bioassay (Promega #J2205). The assay employs TIGIT effector cells that expresses the T cell receptor, CD226, and TIGIT, and CHO-K1 cells expressing CD155. When co-cultured, CD155 binding to TIGIT inhibits CD226 pathway-activated luminescence. When a TIGIT blocking antibody is introduced, the TIGIT/CD155 interaction is blocked, allowing CD155 to bind CD226, and re-establishing CD226 pathway luminescence. TIGIT reporter cells were plated overnight at 37° C. in a 5% CO2 incubator. The next day the antibodies were added to the target cells at a top concentration of 10 ug/ml followed by a dilution series of 9 points plus a no antibody control, the CD155/CHO-K1 cells were added, and the cells were incubated for another 6 hours at 37° C. and 5% CO2. Bio-Glo luciferase substrate was added, incubated for 10 minutes at room temperature, and the luminescence was measured on a Perkin Elmer Envision plate reader. Data were graphed and the $EC_{50}$ for each antibody was determined by curve fitting using GraphPad Prism.

Data for the cohort of 54 antibodies are shown in Tables 3-5, which follow below:

TABLE 3

Mean Fluorescent Intensities (MFI) and ELISA data (for supernatants)

| Clone Name | MFI @ 10 ug/ml | | Elisa OD450 @ 1 ug/ml | | |
|---|---|---|---|---|---|
| | MFI parental cells | MFI hu TIGIT cells | Elisa human TIGIT | Elisa murine TIGIT | Elisa cyno TIGIT |
| 43352p1.A11 | 274 | 8,788 | 0.677 | 0.056 | 0.048 |
| 43352p1.D11 | 309 | 8,648 | 2.153 | 0.046 | 0.044 |
| 43352p1.H8 | 1065 | 10,320 | 1.800 | 1.848 | 0.363 |
| 43586p1.1.A7 | 292 | 8,996 | 2.011 | 0.045 | 1.340 |
| 43586p1.1.C2 | 267 | 6,709 | 1.485 | 0.046 | 0.817 |
| 43586p1.1.G9 | 289 | 8,996 | 2.227 | 0.046 | 1.601 |
| 43586p1.1.H8 | 282 | 9,171 | 1.930 | 0.048 | 1.252 |
| 43586p1.2.A4 | 935 | 13,651 | 1.692 | 1.820 | 0.239 |
| 43586p1.2.B2 | 342 | 9,270 | 2.064 | 2.013 | 1.575 |
| 43586p1.2.B8 | 320 | 9,469 | 2.100 | 1.660 | 1.461 |
| 43586p1.2.C5 | 313 | 10,660 | 2.033 | 2.033 | 0.685 |
| 43586p1.2.C9 | 282 | 8,326 | 2.172 | 0.046 | 1.613 |
| 43586p1.2.C11 | 340 | 9,550 | 2.029 | 2.010 | 1.813 |
| 43586p1.2.C12 | 733 | 11,923 | 2.211 | 2.032 | 1.682 |
| 43586p1.2.E1 | 261 | 9,481 | 2.253 | 2.108 | 1.855 |
| 43586p1.2.E2 | 293 | 9,323 | 2.016 | 1.785 | 1.734 |
| 43586p1.2.E4 | 320 | 9,548 | 2.091 | 2.030 | 1.859 |
| 43586p1.2.E6 | 1011 | 10,468 | 1.824 | 2.012 | 0.776 |
| 43586p1.2.F6 | 412 | 10,674 | 2.066 | 2.086 | 1.728 |
| 43586p1.2.F9 | 319 | 9,108 | 1.996 | 2.136 | 1.708 |
| 43586p1.2.G4 | 272 | 9,337 | 2.025 | 2.039 | 1.884 |
| 43586p1.2.G10 | 339 | 10,135 | 1.989 | 2.104 | 1.517 |
| 43586p2.A03 | 284 | 9,067 | 1.964 | 0.046 | 1.414 |
| 43586p2.B02 | 249 | 9,091 | 1.937 | 0.046 | 1.591 |
| 43586p2.B03 | 252 | 6,113 | 1.161 | 0.047 | 0.047 |
| 43586p2.B05 | 253 | 9,324 | 1.840 | 0.070 | 1.323 |
| 43586p2.C01 | 261 | 7,773 | 1.810 | 0.046 | 1.319 |
| 43586p2.C09 | 330 | 8,828 | 2.071 | 0.046 | 1.787 |
| 43586p2.D01 | 260 | 9,987 | 1.952 | 1.660 | 1.610 |
| 43586p2.D05 | 306 | 9,956 | 1.916 | 1.667 | 1.730 |
| 43586p2.D06 | 363 | 15,432 | 1.775 | 1.362 | 1.657 |
| 43586p2.D11 | 377 | 9,533 | 2.011 | 1.608 | 1.603 |
| 43586p2.E08 | 295 | 11,280 | 1.457 | 2.033 | 1.868 |
| 43586p2.F02 | 257 | 8,959 | 1.855 | 1.897 | 1.767 |
| 43586p2.F10 | 476 | 14,432 | 1.753 | 1.295 | 0.987 |
| 43586p2.F11 | 274 | 9,196 | 1.978 | 1.932 | 1.923 |
| 43586p2.G01 | 300 | 9,722 | 2.033 | 1.953 | 1.145 |
| 43586p2.G02 | 265 | 7,590 | 1.875 | 1.695 | 1.500 |
| 43586p2.G10 | 368 | 9,397 | 2.207 | 2.230 | 1.833 |
| 43586p2.H02 | 295 | 9,133 | 2.004 | 1.933 | 1.092 |
| 43645p1.B2 | 283 | 8,951 | 2.424 | 1.850 | 1.609 |
| 43645p1.B8 | 271 | 9,407 | 1.756 | 0.052 | 1.381 |
| 43645p1.C9 | 298 | 16,481 | 1.858 | 0.065 | 1.392 |
| 43645p1.C11 | 275 | 9,040 | 2.184 | 1.691 | 1.649 |
| 43645p1.D1 | 259 | 9,254 | 2.023 | 0.047 | 1.506 |
| 43645p1.D3 | 256 | 9,352 | 2.130 | 1.898 | 1.741 |
| 43645p1.D7 | 296 | 9,661 | 2.064 | 0.320 | 1.881 |
| 43645p1.D8 | 260 | 10,341 | 1.774 | 0.053 | 1.359 |

TABLE 3-continued

Mean Fluorescent Intensities (MFI) and ELISA data (for supernatants)

| | MFI @ 10 ug/ml | | Elisa OD450 @ 1 ug/ml | | |
|---|---|---|---|---|---|
| Clone Name | MFI parental cells | MFI hu TIGIT cells | Elisa human TIGIT | Elisa murine TIGIT | Elisa cyno TIGIT |
| 43645p1.E3 | 245 | 9,952 | 1.993 | 0.947 | 1.528 |
| 43645p1.F7 | 270 | 15,401 | 1.968 | 0.489 | 1.517 |
| 43645p1.F11 | 302 | 10,894 | 2.027 | 1.855 | 1.805 |
| 43645p1.F12 | 272 | 4,103 | 0.477 | 0.052 | 0.069 |
| 43645p1.G5 | 307 | 12,379 | 1.936 | 1.010 | 1.726 |
| 43645p1.H10 | 267 | 10,021 | 2.005 | 1.698 | 1.848 |

TABLE 4

Antibody kinetics and binning data

| | kinetics | | | | | |
|---|---|---|---|---|---|---|
| Clone Name | KD (M) human TIGIT | KD (M) cyno TIGIT | KD (M) cyno repeat | KD (M) murine TIGIT | KD (M) murine repeat | binning epitope bin |
| 43352p1.A11 | 7.16E−11 | N/A | | N/A | | 2 |
| 43352p1.D11 | 6.85E−11 | N/A | | N/A | | 2 |
| 43352p1.H8 | 1.94E−10 | 1.20E−07 | 1.14E−07 | 1.14E−09 | 7.40E−10 | 2 |
| 43586p1.1.A7 | 7.21E−10 | 2.00E−08 | | N/A | | 2 |
| 43586p1.l.C2 | 3.83E−10 | 3.69E−09 | | N/A | | 1 |
| 43586p1.l.G9 | 1.08E−09 | 1.88E−08 | | N/A | | 2 |
| 43586p1.l.H8 | 2.92E−10 | 3.16E−08 | 1.60E−08 | N/A | | 2 |
| 43586p1.2.A4 | N/A | N/A | | N/A | | 2 |
| 43586p1.2.B2 | 2.45E−10 | 1.43E−08 | 1.80E−09 | 3.28E−09 | 1.30E−09 | 2 |
| 43586p1.2.B8 | 1.25E−10 | 2.53E−08 | | 5.01E−07 | | 2 |
| 43586p1.2.C5 | 1.04E−09 | 4.11E−07 | | 3.20E−09 | | 2 |
| 43586p1.2.C9 | 2.02E−10 | 8.69E−09 | | 3.66E−09 | | 2 |
| 43586p1.2.C11 | 5.17E−11 | 2.56E−09 | 1.90E−09 | 1.45E−09 | 1.80E−09 | 2 |
| 43586p1.2.C12 | 1.92E−10 | 9.18E−09 | | 6.82E−08 | | 2 |
| 43586p1.2.E1 | 2.90E−11 | 6.27E−09 | 3.20E−09 | 7.34E−09 | 2.20E−08 | 2 |
| 43586p1.2.E2 | 4.86E−11 | 9.50E−09 | 4.80E−09 | 1.22E−07 | 6.70E−08 | 2 |
| 43586p1.2.E4 | 1.17E−10 | 2.54E−08 | 2.80E−09 | 6.65E−08 | 1.80E−08 | 2 |
| 43586p1.2.E6 | 1.56E−09 | 5.64E−07 | | 3.07E−09 | | 2 |
| 43586p1.2.F6 | 2.23E−10 | 3.81E−08 | 4.60E−09 | 5.38E−06 | 6.20E−08 | 2 |
| 43586p1.2.F9 | 3.38E−10 | 1.22E−08 | 2.00E−09 | 4.95E−09 | 2.10E−09 | 2 |
| 43586p1.2.G4 | 3.94E−10 | 3.19E−09 | 5.82E−10 | 6.89E−09 | 4.80E−09 | 2 |
| 43586p1.2.G10 | 9.41E−10 | 1.40E−08 | 6.30E−09 | 1.56E−08 | 1.00E−08 | 2 |
| 43586p2.A03 | 3.86E−10 | 6.30E−08 | 3.30E−08 | N/A | | 2 |
| 43586p2.B02 | 2.19E−09 | 2.68E−08 | | N/A | | 2 |
| 43586p2.B03 | 6.73E−08 | N/A | | N/A | | 2 |
| 43586p2.B05 | 1.19E−10 | N/A | | N/A | | 1 |
| 43586p2.C01 | 1.51E−10 | N/A | | N/A | | 1 |
| 43586p2.C09 | 3.54E−10 | 2.62E−09 | | N/A | | 2 |
| 43586p2.D01 | 1.04E−09 | 2.91E−08 | | 4.96E−10 | | 2 |
| 43586p2.D05 | 2.14E−10 | 1.55E−09 | | 5.46E−09 | | 2 |
| 43586p2.D06 | 3.44E−10 | 1.06E−09 | | 3.09E−09 | | 1 |
| 43586p2.D11 | 5.58E−10 | 8.74E−08 | 4.40E−09 | 4.14E−08 | 7.44E−10 | 2 |
| 43586p2.E08 | 2.52E−10 | 1.83E−09 | | 5.79E−09 | | 2 |
| 43586p2.F02 | 1.81E−09 | 1.44E−08 | | 9.60E−08 | | 2 |
| 43586p2.F10 | N/A | N/A | | N/A | | 2 |
| 43586p2.F11 | 3.07E−10 | 2.09E−09 | | 6.23E−09 | | 2 |
| 43586p2.G01 | 2.69E−09 | 3.39E−07 | | 1.65E−09 | | 2 |
| 43586p2.G02 | 6.39E−10 | 2.37E−09 | | 1.57E−09 | | 1 |
| 43586p2.G10 | 2.67E−10 | N/A | 3.7E−09 | 3.05E−09 | 9.19E−10 | 2 |
| 43586p2.H02 | 2.53E−09 | 3.34E−07 | | 3.94E−09 | | 2 |
| 43645p1.B2 | 4.64E−11 | N/A | 9.3E−10 | N/A | 4.20E−08 | 2 |
| 43645p1.B8 | 9.06E−11 | N/A | | N/A | | 1 |
| 43645p1.C9 | 1.95E−10 | 2.35E−08 | | N/A | | 1 |
| 43645p1.C11 | 8.88E−11 | N/A | | N/A | | 2 |
| 43645p1.D1 | 3.43E−10 | 1.76E−08 | 2.90E−09 | N/A | 1.40E−08 | 2 |
| 43645p1.D3 | 1.71E−11 | N/A | 3.2E−10 | N/A | 1.90E−08 | 2 |
| 43645p1.D7 | 6.76E−09 | 6.27E−09 | | N/A | | 2 |
| 43645p1.D8 | 4.16E−10 | 2.45E−08 | 1.90E−09 | N/A | | 2 |
| 43645p1.E3 | 2.67E−11 | 6.96E−09 | 5.50E−09 | N/A | | 2 |
| 43645p1.F7 | 7.41E−11 | N/A | | N/A | | 1 |
| 43645p1.F11 | 3.22E−10 | 3.30E−08 | 1.60E−08 | 2.35E−07 | 9.10E−08 | 2 |
| 43645p1.F12 | N/A | N/A | | N/A | | 2 |
| 43645p1.G5 | 5.07E−11 | N/A | 3.68E−10 | N/A | | 2 |

TABLE 4-continued

| Antibody kinetics and binning data | | | | | | |
|---|---|---|---|---|---|---|
| | kinetics | | | | | |
| Clone Name | KD (M) human TIGIT | KD (M) cyno TIGIT | KD (M) cyno repeat | KD (M) murine TIGIT | KD (M) murine repeat | binning epitope bin |
| 43645p1.H10 | 1.28E−10 | N/A | 1.81E−10 | N/A | 5.95E−10 | 2 |
| benchmark 22G2 | 2.02E−10 | 1.61E−08 | 3.40E−09 | N/A | | 2 |

TABLE 5

| Functional assays data. Antibody 22G2) is a control antibody that bids to TIGIT. | | | |
|---|---|---|---|
| | functional assay | | |
| Clone Name | blocking activity | EC50 TIGIT blocking assay | max. signal (% of 22G2) |
| 43352p1.A11 | Y | 0.401 | 101 |
| 43352p1.D11 | Y | 0.348 | 105 |
| 43352p1.H8 | Y | 0.542 | 96 |
| 43586p1.1.A7 | Y | 0.635 | 89 |
| 43586p1.1.C2 | N | | |
| 43586p1.1.G9 | Y | 0.991 | 113 |
| 43586p1.1.H8 | Y | 0.408 | 124 |
| 43586p1.2.A4 | N | | |
| 43586p1.2.B2 | Y | 0.427 | 121 |
| 43586p1.2.B8 | Y | 0.282 | 130 |
| 43586p1.2.C5 | Y | 0.817 | 91 |
| 43586p1.2.C9 | Y | 0.451 | 126 |
| 43586p1.2.C11 | Y | 0.365 | 106 |
| 43586p1.2.C12 | Y | 0.487 | 118 |
| 43586p1.2.E1 | Y | 0.427 | 111 |
| 43586p1.2.E2 | Y | 0.285 | 125 |
| 43586p1.2.E4 | Y | 0.278 | 113 |
| 43586p1.2.E6 | Y | 0.718 | 97 |
| 43586p1.2.F6 | Y | 0.205 | 116 |
| 43586p1.2.F9 | Y | 0.363 | 127 |
| 43586p1.2.G4 | Y | 0.337 | 101 |
| 43586p1.2.G10 | Y | 0.497 | 96 |
| 43586p2.A03 | Y | 0.591 | 109 |
| 43586p2.B02 | Y | 1.168 | 106 |
| 43586p2.B03 | N | | |
| 43586p2.B05 | N | | |
| 43586p2.C01 | N | | |
| 43586p2.C09 | Y | 0.651 | 115 |
| 43586p2.D01 | Y | 1.150 | 103 |
| 43586p2.D05 | Y | 0.531 | 118 |
| 43586p2.D06 | N | | |
| 43586p2.D11 | Y | 0.559 | 102 |
| 43586p2.E08 | Y | 0.562 | 117 |
| 43586p2.F02 | Y | 0.536 | 92 |
| 43586p2.F10 | N | | |
| 43586p2.F11 | Y | 0.483 | 104 |
| 43586p2.G01 | Y | 3.152 | 110 |
| 43586p2.G02 | N | | |
| 43586p2.G10 | Y | 0.676 | 99 |
| 43586p2.H02 | Y | 1.330 | 80 |
| 43645p1.B2 | Y | 0.315 | 111 |
| 43645p1.B8 | N | | |
| 43645p1.C9 | N | | |
| 43645p1.C11 | Y | 0.376 | 119 |
| 43645p1.D1 | Y | 0.260 | 111 |
| 43645p1.D3 | Y | 0.375 | 115 |
| 43645p1.D7 | Y | 2.682 | 57 |
| 43645p1.D8 | Y | 0.284 | 108 |
| 43645p1.E3 | Y | 0.364 | 103 |
| 43645p1.F7 | N | | |
| 43645p1.F11 | Y | 0.324 | 100 |
| 43645p1.F12 | N | | |

TABLE 5-continued

| Functional assays data. Antibody 22G2) is a control antibody that bids to TIGIT. | | | |
|---|---|---|---|
| | functional assay | | |
| Clone Name | blocking activity | EC50 TIGIT blocking assay | max. signal (% of 22G2) |
| 43645p1.G5 | Y | 0.264 | 99 |
| 43645p1.H10 | Y | 0.582 | 109 |
| benchmark 22G2 | Y | 0.683 | 100 |

Based on the data shown above, a total of 8 antibodies were selected, each from a different clade. These antibodies bind to both human and cynomolgus TIGIT and having an EC50 of <0.4 in each assay. The selected antibodies were: 43586p1.2.C11 (Heavy Chain CDRs 1-3 are SEQ ID NOs: 109-111, respectively; and Light Chain CDRs 1-3 are SEQ ID NOs: 133-135), 43586p1.2.G04 (Heavy Chain CDRs 1-3 are SEQ ID NOs: 112-114, respectively; and Light Chain CDRs 1-3 are SEQ ID NOs: 136-138), 43586p1.2.F06 (Heavy Chain CDRs 1-3 are SEQ ID NOs: 115-117, respectively; and Light Chain CDRs 1-3 are SEQ ID NOs: 139-141), 43586p1.2.E04 (Heavy Chain CDRs 1-3 are SEQ ID NOs: 118-120, respectively; and Light Chain CDRs 1-3 are SEQ ID NOs: 142-144), 43586p1.1.H08 (Heavy Chain CDRs 1-3 are SEQ ID NOs: 121-123, respectively; and Light Chain CDRs 1-3 are SEQ ID NOs: 145-147), 43645p1.B02 (Heavy Chain CDRs 1-3 are SEQ ID NOs: 124-126, respectively; and Light Chain CDRs 1-3 are SEQ ID NOs: 148-150), 43645p1.G05 (Heavy Chain CDRs 1-3 are SEQ ID NOs: 127-129, respectively; and Light Chain CDRs 1-3 are SEQ ID NOs: 151-153), and 43645p1.DO1 (Heavy Chain CDRs 1-3 are SEQ ID NOs: 130-132, respectively; and Light Chain CDRs 1-3 are SEQ ID NOs: 154-156).

The antibodies were tested in a TIGIT/CD155 blockade bioassay (Promega), which is a cell-based assay designed to measure the potency and stability of the antibodies in blocking the TIGIT/CD155 interaction. The assay consists of two genetically engineered cell lines: (a) TIGIT Effector Cells: Jurkat T cells expressing human TIGIT with a luciferase reporter driven by a native promoter that can respond to both TCR activation and CD226 co-stimulation and (b) CD155 aAPC/CHO-K1 Cells: CHO-K1 cells engineered to express human CD155 with an engineered cell-surface protein designed to activate the TCR complex in an antigen-independent manner.

Figure 4:
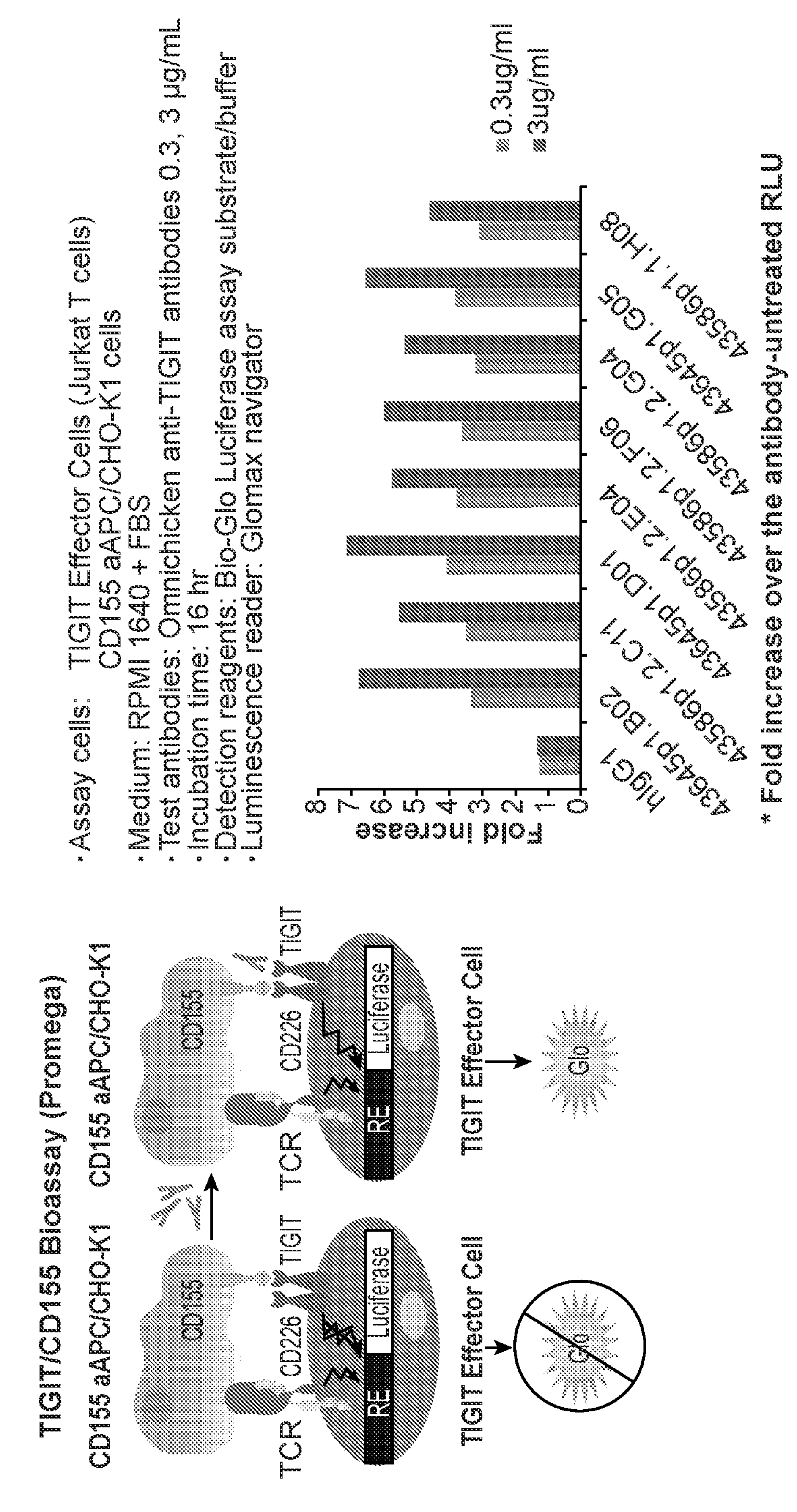
FIG. 4 shows the results of a TIGIT/CD155 bioassay on 8 selected antibodies.

When the two cell types are co-cultured, TIGIT inhibits CD226 activation and promoter-mediated luminescence. Addition of an anti-TIGIT antibody blocks the interaction of TIGIT with CD155 or inhibits the ability of TIGIT to prevent CD226 homodimerization, resulting in promoter-mediated luminescence. This luminescence can be measured to identify how well an antibody inhibits binding to CD155. This assay is illustrated in FIG. 4. The results of the assay are also illustrated in FIG. 4. A similar assay was performed to test whether an antibody inhibits binding of TIGIT to CD112. This assay and the results are shown in FIG. 5.

FIG. 6 summarizes the results of several assays. Antibody 43586p1.2.F06 was selected for future assays since it worked well in both cellular assays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An antibody that binds to TIGIT, wherein the antibody comprises a heavy chain variable domain (VH) and a light chain variable domain (VL) comprising:

(a) heavy chain CDR1, CDR2 and CDR3 regions comprising amino acid sequences GFTFDDY (SEO ID NO: 109), NWNGDK (SEO ID NO: 110), and HWIVFOYGMDV (SEO ID NO: 111), respectively, and light chain CDR1, CDR2 and CDR3 regions comprising amino acid sequences SGSISNIETKYVSW (SEO ID NO: 133), NSDORPS (SEO ID NO: 134), and VSWDASLKSW (SEO ID NO: 135), respectively;

(b) heavy chain CDR1, CDR2 and CDR3 regions comprising amino acid sequences GFTFDDY (SEO ID NO: 112), NWNGDK (SEO ID NO: 113) and HWIVFOYGLDV (SEO ID NO: 114), respectively, and light chain CDR1, CDR2 and CDR3 regions comprising amino acid sequences SGVSSNIEI KYVSW (SEO ID NO: 136), NSHORPS (SEO ID NO: 137), TSWDDRLKSW (SEO ID NO: 138), respectively;

(c) heavy chain CDR1, CDR2 and CDR3 regions comprising amino acid sequences GFTFTSY (SEO ID NO: 115), TWDGDR (SEO ID NO: 116) and HWTVFOYGMDV (SEO ID NO: 117), respectively, and light chain CDR1, CDR2 and CDR3 regions comprising amino acid sequences SGTISNIET KYVSW (SEO ID NO: 139), GNHORPS (SEO ID NO: 140) and ASWENDLKSW (SEO ID NO: 141), respectively;

(d) heavy chain CDR1, CDR2 and CDR3 regions comprising amino acid sequences GFTFSDY (SEO ID NO: 118), TWDGDR (SEO ID NO: 119) and HWTVFOYGMDV (SEO ID NO: 120), respectively, and light chain CDR1, CDR2 and CDR3 regions comprising amino acid sequences SGTISNIEIKYVSW (SEO ID NO: 142), GNHORPS (SEO ID NO: 143) and SSWENDLKSW (SEO ID NO: 144), respectively;

(e) heavy chain CDR1, CDR2 and CDR3 regions comprising amino acid sequences GFTFIDF (SEO ID NO: 121), SWIGDT (SEO ID NO: 122) and HWTVYOYGMDV (SEO ID NO: 123), respectively, and light chain CDR1, CDR2 and CDR3 regions comprising amino acid sequences SGSTSDIET KYVSW (SEO ID NO: 145), GNHORPS (SEO ID NO: 146) and TAWDNTLKSW (SEO ID NO: 147), respectively;

(f) heavy chain CDR1, CDR2 and CDR3 regions comprising amino acid sequences GFTFSSY (SEO ID NO: 124), HISDS (SEO ID NO: 125) and GHTVLOYGMDV (SEO ID NO: 126), respectively, and light chain CDR1, CDR2 and CDR3 regions comprising amino acid sequences SGDISNTRNNYVSW (SEO ID NO: 148), GNHORPS (SEO ID NO: 149) and GTWDNTLNAW (SEO ID NO: 150), respectively;

(g) heavy chain CDR1, CDR2 and CDR3 regions comprising amino acid sequences GFTFSSY (SEO ID NO: 127), SIFSGDS (SEO ID NO: 128) and SHTVLOYGMDV (SEO ID NO: 129), respectively, and light chain CDR1, CDR2 and CDR3 regions comprising amino acid sequences SGVTSNIR NYYVSW (SEO ID NO: 151), GNDORPS (SEO ID NO: 152) and GTWDNTLNAW (SEO ID NO: 153), respectively; or (h) heavy chain CDR1, CDR2 and CDR3 regions comprising amino acid sequences GFSFWGY (SEO ID NO: 130), AGNSY (SEO ID NO: 131) and DRSFYNYYDIDV (SEO ID NO: 132), respectively, and light chain CDR1, CDR2 and CDR3 regions comprising amino acid sequences SGTNSNIGSNHVNW (SEO ID NO: 154), TNNORPS (SEO ID NO: 155) and AAWDGSLNGW (SEO ID NO: 156), respectively.

2. The antibody of claim 1, wherein the antibody comprises:

(a) a heavy chain variable domain comprising an amino acid sequence that is at least 90% identical to SEO ID NO: 13 and a light chain variable domain comprising an amino acid sequence that is at least 90% identical to SEO ID NO: 67, (b) a heavy chain variable domain comprising an amino acid sequence that is at least 90% identical to SEO ID NO: 2; and a light chain variable domain comprising an amino acid sequence that is at least 90% identical to SEO ID NO: 75, (c) a heavy chain variable domain comprising an amino acid sequence that is at least 90% identical to SEO ID NO: 19 and a light chain variable domain comprising an amino acid sequence that is at least 90% identical to SEO ID NO: 73, (d) a heavy chain variable domain comprising an amino acid sequence that is at least 90% identical to SEO ID NO: 17 and a light chain variable domain comprising an amino acid sequence that is at least 90% identical to SEO ID NO: 71, (e) a heavy chain variable domain comprising an amino acid sequence that is at least 90% identical to SEO ID NO: 7 and a light chain variable domain comprising an amino acid sequence that is at least 90% identical to SEO ID NO: 61, (f) a heavy chain variable domain comprising an amino acid sequence that is at least 90% identical to SEO ID NO: 41 and a light chain variable domain comprising an amino acid sequence that is at least 90% identical to SEO ID NO: 95, (g) a heavy chain variable domain comprising an amino acid sequence that is at least 90% identical to SEO ID NO: 53 and a light chain variable domain comprising an amino acid sequence that is at least 90% identical to SEO ID NO: 107, or (h) a heavy chain variable domain comprising an amino acid sequence that is at least 90% identical to SEO ID NO: 45; and a light chain variable domain comprising an amino acid sequence that is at least 90% identical to SEO ID NO: 99.

3. The antibody of claim 1, wherein the antibody comprises a VH of SEQ ID NO: 19 and a VL of SEQ ID NO: 73.

4. The antibody of claim 1, wherein the heavy chain variable domain and the light chain variable domain are present in separate polypeptides.

5. The antibody of claim 1, wherein the heavy chain variable domain and the light chain variable domain are present in a single polypeptide.

6. The antibody of claim 1, wherein the antibody binds TIGIT with an affinity in the range of 107 M-1 to 1012 M-1.

7. The antibody of claim 1, wherein the antibody comprises a covalently linked non-peptide synthetic polymer.

8. The antibody of claim 7, wherein the synthetic polymer is poly(ethylene glycol) polymer.

9. The antibody of claim 1, wherein the antibody comprises a covalently linked lipid or fatty acid moiety.

10. The antibody of claim 1, wherein the antibody comprises a covalently linked polysaccharide or carbohydrate moiety.

11. The antibody of claim 1, wherein the antibody is a single chain Fv (scFv) antibody.

12. The antibody of claim 11, wherein the scFv is multimerized.

13. A pharmaceutical composition comprising:

a) the antibody of claim 1; and b) a pharmaceutically acceptable carrier.

14. The pharmaceutical composition of claim 13, wherein the antibody is encapsulated in a liposome.

15. A method of treating cancer, comprising administering to a cancer patient an effective amount of the antibody of claim 1, wherein the cancer patient has cancer, and wherein the cancer is melanoma of the skin, non-small cell lung cancer, kidney cancer, bladder cancer, colorectal carcinoma, head and neck cancer, or Hodgkin lymphoma.

16. The method of claim 15, wherein the cancer patient is also being treated or has been treated with an immune checkpoint inhibitor.

17. The method of claim 16, wherein the immune checkpoint inhibitor is a PD-1/PD-L1 inhibitor.

18. An antibody that binds to TIGIT, wherein the antibody comprises a VH and a VL comprising:

(i) heavy chain CDR1, CDR2 and CDR3 regions comprising amino acid sequences GFTFTSY (SEQ ID NO: 115), TWDGDR (SEQ ID NO: 116) and HWTVFQYGMDV (SEQ ID NO: 117), respectively, and (ii) light chain CDR1, CDR2 and CDR3 regions comprising amino acid sequences SGTISNIETKYVSW (SEQ ID NO:139), GNHQRPS (SEQ ID NO: 140) and ASWENDLKSW (SEQ ID NO: 141), respectively.

* * * * *

SEQUENCE LISTING

```
<160> NUMBER OF SEQ ID NOS: 156

<210> SEQ ID NO 1
<211> LENGTH: 119
<212> TYPE: PRT
<213> ORGANISM: Gallus gallus

<400> SEQUENCE: 1

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Glu Gly Leu Glu Trp Val
        35                  40                  45

Ser Leu Thr Ser Gly Asn Gly Val Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ile Tyr Tyr Cys
                85                  90                  95

Ala Arg Gly Thr Tyr Leu Ile Ser Phe Phe Asp Tyr Trp Gly Leu Gly
            100                 105                 110

Thr Leu Val Thr Val Ser Ser
        115


<210> SEQ ID NO 2
<211> LENGTH: 119
<212> TYPE: PRT
<213> ORGANISM: Gallus gallus

<400> SEQUENCE: 2

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Glu Gly Leu Glu Trp Val
        35                  40                  45

Ser Leu Ile Ser Gly Asn Gly Val Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ile Tyr Tyr Cys
                85                  90                  95

Ala Arg Gly Thr Tyr Leu Ile Ser Phe Phe Asp Tyr Trp Gly Leu Gly
            100                 105                 110

Thr Leu Val Thr Val Ser Ser
        115
```

<210> SEQ ID NO 3
<211> LENGTH: 121
<212> TYPE: PRT
<213> ORGANISM: Gallus gallus

<400> SEQUENCE: 3

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Asn Phe Ser Thr Tyr
            20                  25                  30

Ala Met Asn Trp Val Arg Gln Ala Pro Gly Glu Gly Leu Glu Trp Val
        35                  40                  45

Ser Gly Ile Ser Gly Arg Ser Ser Gly Asp Thr Thr Tyr Tyr Ala Asp
    50                  55                  60

Ser Val Arg Gly Trp Phe Thr Val Ser Arg Asp Asn Ser Lys Asn Thr
65                  70                  75                  80

Leu Tyr Leu Gln Met Ser Ser Leu Arg Ala Glu Asp Thr Ala Val Tyr
                85                  90                  95

Tyr Cys Ala Arg Glu Thr Trp Ile Arg Gly Tyr Phe Asp Tyr Trp Gly
            100                 105                 110

Leu Gly Thr Leu Val Thr Val Ser Ser
        115                 120
```

<210> SEQ ID NO 4
<211> LENGTH: 125
<212> TYPE: PRT
<213> ORGANISM: Gallus gallus

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Gly Ile Ser Tyr Asp Gly Ser Ile Gln Tyr Tyr Ala Asp Ser Val
    50                  55                  60

Lys Gly Arg Leu Thr Ile Ser Arg Asp Asn Ser Lys Asn Thr Leu Asn
65                  70                  75                  80

Leu Gln Met Asn Ser Leu Arg Ala Gly Asp Thr Ala Val Tyr Tyr Cys
                85                  90                  95

Ala Lys His Leu Thr Gly Gly Thr Thr Asp Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 5
<211> LENGTH: 121
<212> TYPE: PRT
<213> ORGANISM: Gallus gallus

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

Tyr Met Asn Trp Val Arg Gln Ala Pro Gly Lys Gly Leu Glu Trp Val
35 40 45

Ser Ser Ile Asn Trp Asn Gly Gly Thr Thr Tyr Tyr Ala Asp Ser Val
50 55 60

Lys Gly Arg Phe Thr Ile Ser Arg Asp Asn Ser Arg Asn Thr Leu Tyr
65 70 75 80

Leu Gln Met Asn Ser Leu Arg Ala Glu Asp Thr Ala Val Tyr Tyr Cys
85 90 95

Ala Lys Asp Gln Asn Trp Asn Phe Tyr Tyr Gly Met Asp Val Trp Gly
100 105 110

Gln Gly Thr Thr Val Thr Val Ser Ser
115 120

<210> SEQ ID NO 6
<211> LENGTH: 124
<212> TYPE: PRT
<213> ORGANISM: Gallus gallus

<400> SEQUENCE: 6

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Thr Tyr
20 25 30

Ala Met Ser Trp Val Arg Gln Ala Pro Gly Lys Gly Leu Glu Trp Val
35 40 45

Ala Gly Ile Ser Tyr Ile Gly Ser Asp Lys Tyr Tyr Ala Asp Ser Val
50 55 60

Lys Gly Arg Leu Thr Ile Ser Arg Asp Asn Ser Lys Asn Thr Leu Tyr
65 70 75 80

Leu Gln Met Asp Ser Leu Arg Ala Glu Asp Thr Ala Val Tyr Tyr Cys
85 90 95

Ala Lys His Leu Thr Gly Gly Thr Thr Asp Tyr Tyr Tyr Tyr Gly Met
100 105 110

Asp Val Trp Gly Gln Gly Thr Thr Val Thr Val Ser
115 120

<210> SEQ ID NO 7
<211> LENGTH: 120
<212> TYPE: PRT
<213> ORGANISM: Gallus gallus

<400> SEQUENCE: 7

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ile Asp Phe
20 25 30

Trp Met Ser Trp Val Arg Gln Ala Pro Gly Lys Gly Leu Glu Trp Val
35 40 45

Ser Ala Ile Ser Trp Ile Gly Asp Thr Tyr Tyr Tyr Ala Asp Ser Val
50 55 60

Lys Gly Arg Phe Thr Val Ser Arg Asp Asn Ser Lys Asn Thr Val Tyr
65 70 75 80

Leu Gln Met Asn Ser Leu Arg Ala Glu Asp Thr Ala Val Tyr Tyr Cys
85 90 95

Ala Lys His Trp Thr Val Tyr Gln Tyr Gly Met Asp Val Trp Gly Gln
100 105 110

```
Gly Thr Thr Val Thr Val Ser Ser
        115                 120


<210> SEQ ID NO 8
<211> LENGTH: 119
<212> TYPE: PRT
<213> ORGANISM: Gallus gallus

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp His
            20                  25                  30

His Met Ser Trp Val Arg Gln Ala Pro Gly Lys Gly Leu Glu Trp Val
        35                  40                  45

Ser Gly Ile Asp Pro Gly Gly Lys Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gln Tyr Asp Trp Asn Asp Asp Met Asp Val Trp Gly Gln Gly
            100                 105                 110

Thr Thr Val Thr Val Ser Ser
        115


<210> SEQ ID NO 9
<211> LENGTH: 120
<212> TYPE: PRT
<213> ORGANISM: Gallus gallus

<400> SEQUENCE: 9

Glu Met Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys His Trp Ile Val Phe Gln Tyr Gly Met Asp Val Trp Gly Gln
            100                 105                 110

Gly Thr Thr Val Thr Val Ser Ser
        115                 120


<210> SEQ ID NO 10
<211> LENGTH: 120
<212> TYPE: PRT
<213> ORGANISM: Gallus gallus

<400> SEQUENCE: 10

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Thr Ser Tyr
            20                  25                  30

Leu Met Ser Trp Val Arg Gln Ala Pro Gly Lys Gly Leu Glu Trp Val
        35                  40                  45

Ser Thr Ile Thr Trp Asp Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Gly Asp Thr Ala Val Tyr Tyr Cys
                85                  90                  95

Ala Lys His Trp Thr Val Phe Gln Tyr Gly Met Asp Val Trp Gly Gln
            100                 105                 110

Gly Thr Thr Val Thr Val Ser Ser
        115                 120


<210> SEQ ID NO 11
<211> LENGTH: 118
<212> TYPE: PRT
<213> ORGANISM: Gallus gallus

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp His
            20                  25                  30

Tyr Met Ser Trp Val Arg Gln Ala Pro Gly Lys Gly Leu Glu Trp Val
        35                  40                  45

Ser Thr Thr Ser Ser Thr Ser Trp Lys Asn Tyr Thr Tyr Tyr Ala Asp
    50                  55                  60

Ser Val Lys Gly Arg Phe Ser Ile Ser Arg Asp Asn Ser Glu Asn Thr
65                  70                  75                  80

Leu Tyr Leu Gln Met Asn Gly Leu Arg Ala Glu Asp Thr Ala Val Tyr
                85                  90                  95

Tyr Cys Ala Lys Gly Ser Tyr Gly Met Asp Val Trp Gly Gln Gly Thr
            100                 105                 110

Thr Val Thr Val Ser Ser
        115


<210> SEQ ID NO 12
<211> LENGTH: 120
<212> TYPE: PRT
<213> ORGANISM: Gallus gallus

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95
```

Ala Lys His Trp Ile Val Phe Gln Tyr Gly Met Asp Val Trp Gly Gln
100 105 110

Gly Thr Thr Val Thr Val Ser Ser
115 120

<210> SEQ ID NO 13
<211> LENGTH: 120
<212> TYPE: PRT
<213> ORGANISM: Gallus gallus

<400> SEQUENCE: 13

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Val Met Ser Trp Val Arg Gln Ala Pro Gly Lys Gly Leu Glu Trp Val
35 40 45

Ser Leu Ile Asn Trp Asn Gly Asp Lys Thr Tyr Cys Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Lys His Trp Ile Val Phe Gln Tyr Gly Met Asp Val Trp Gly Gln
100 105 110

Gly Thr Thr Val Thr Val Ser Ser
115 120

<210> SEQ ID NO 14
<211> LENGTH: 115
<212> TYPE: PRT
<213> ORGANISM: Gallus gallus

<400> SEQUENCE: 14

Glu Ser Gly Gly Gly Leu Val Gln Pro Gly Gly Ser Leu Arg Leu Ser
1 5 10 15

Cys Ala Ala Ser Gly Phe Thr Phe Ser Asp Tyr Leu Met Thr Trp Val
20 25 30

Arg Gln Ala Pro Gly Lys Gly Leu Glu Trp Val Ser Thr Ile Thr Trp
35 40 45

Asp Gly Asp Arg Thr Tyr Tyr Ala Asp Ser Val Lys Gly Arg Phe Thr
50 55 60

Ile Ser Arg Asp Asn Ser Lys Asn Thr Leu Tyr Leu Gln Met Asn Ser
65 70 75 80

Leu Arg Ala Glu Asp Thr Ala Val Tyr Tyr Cys Ala Lys His Trp Thr
85 90 95

Val Phe Gln Tyr Gly Met Asp Val Trp Gly Gln Gly Thr Thr Val Thr
100 105 110

Val Ser Ser
115

<210> SEQ ID NO 15
<211> LENGTH: 120
<212> TYPE: PRT
<213> ORGANISM: Gallus gallus

<400> SEQUENCE: 15

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Leu Met Thr Trp Val Arg Gln Ala Pro Gly Lys Glu Leu Glu Trp Val
35 40 45

Ser Thr Ile Thr Trp Asp Gly Asp Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Trp Thr Val Phe Gln Tyr Gly Met Asp Val Trp Gly Gln
100 105 110

Gly Thr Thr Val Thr Val Ser Ser
115 120

<210> SEQ ID NO 16
<211> LENGTH: 120
<212> TYPE: PRT
<213> ORGANISM: Gallus gallus

<400> SEQUENCE: 16

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Ser Tyr
20 25 30

Leu Met Ser Trp Val Arg Gln Ala Pro Gly Lys Gly Leu Glu Trp Val
35 40 45

Ser Thr Ile Thr Trp Asp Gly Asp Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Gly Asp Thr Ala Val Tyr Tyr Cys
85 90 95

Ala Lys His Trp Thr Val Phe Gln Tyr Gly Met Asp Val Trp Gly Gln
100 105 110

Gly Thr Thr Val Thr Val Ser Ser
115 120

<210> SEQ ID NO 17
<211> LENGTH: 120
<212> TYPE: PRT
<213> ORGANISM: Gallus gallus

<400> SEQUENCE: 17

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Leu Met Thr Trp Val Arg Gln Ala Pro Gly Lys Gly Leu Glu Trp Val
35 40 45

Ser Thr Ile Thr Trp Asp Gly Asp Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Trp Thr Val Phe Gln Tyr Gly Met Asp Val Trp Gly Gln
100 105 110

Gly Thr Thr Val Thr Val Ser Ser
115 120

<210> SEQ ID NO 18
<211> LENGTH: 118
<212> TYPE: PRT
<213> ORGANISM: Gallus gallus

<400> SEQUENCE: 18

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Asp His
20 25 30

Tyr Met Ser Trp Val Arg Gln Ala Pro Gly Lys Gly Leu Glu Trp Val
35 40 45

Ser Thr Thr Ser Ser Thr Ser Trp Lys Asn Tyr Thr Tyr Tyr Ala Asp
50 55 60

Ser Val Lys Gly Arg Phe Ser Ile Ser Arg Asp Asn Ser Glu Asn Thr
65 70 75 80

Leu Tyr Leu Gln Met Asn Gly Leu Arg Ala Glu Asp Thr Ala Val Tyr
85 90 95

Tyr Cys Ala Lys Gly Ser Tyr Gly Met Asp Val Trp Gly Gln Gly Thr
100 105 110

Thr Val Thr Val Ser Ser
115

<210> SEQ ID NO 19
<211> LENGTH: 120
<212> TYPE: PRT
<213> ORGANISM: Gallus gallus

<400> SEQUENCE: 19

Glu Val Gln Leu Leu Glu Ser Gly Glu Gly Leu Val Gln Pro Gly Gly
1 5 10 15

Ser Leu Arg Leu Ser Cys Ala Ala Ser Gly Phe Thr Phe Thr Ser Tyr
20 25 30

Leu Met Ser Trp Val Arg Gln Ala Pro Gly Lys Gly Leu Glu Trp Val
35 40 45

Ser Thr Ile Thr Trp Asp Gly Asp Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Val Gly Asp Thr Ala Val Tyr Tyr Cys
85 90 95

Ala Lys His Trp Thr Val Phe Gln Tyr Gly Met Asp Val Trp Gly Gln
100 105 110

Gly Thr Thr Val Thr Val Ser Ser
115 120

<210> SEQ ID NO 20
<211> LENGTH: 120

<212> TYPE: PRT
<213> ORGANISM: Gallus gallus

<400> SEQUENCE: 20

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Val Met Ser Trp Val Arg Gln Ala Pro Gly Lys Gly Leu Glu Trp Val
35 40 45

Ser Leu Ile Asn Trp Asn Gly Asp Lys Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Lys His Trp Ile Val Phe Gln Tyr Gly Met Asp Val Trp Gly Arg
100 105 110

Gly Thr Thr Val Thr Val Ser Ser
115 120

<210> SEQ ID NO 21
<211> LENGTH: 120
<212> TYPE: PRT
<213> ORGANISM: Gallus gallus

<400> SEQUENCE: 21

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Val Met Ser Trp Val Arg Gln Ala Pro Gly Lys Gly Leu Glu Trp Val
35 40 45

Ser Leu Ile Asn Trp Asn Gly Asp Lys Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Trp Ile Val Phe Gln Tyr Gly Leu Asp Val Trp Gly Gln
100 105 110

Gly Thr Thr Val Thr Val Ser Ser
115 120

<210> SEQ ID NO 22
<211> LENGTH: 120
<212> TYPE: PRT
<213> ORGANISM: Gallus gallus

<400> SEQUENCE: 22

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Val Met Ser Trp Val Arg Gln Ala Pro Gly Lys Glu Leu Glu Trp Val
35 40 45

```
Ser Leu Ile Asn Trp Asn Gly Asp Lys Thr Cys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys His Trp Ile Val Phe Gln Tyr Gly Met Asp Val Trp Gly Gln
            100                 105                 110

Gly Thr Thr Val Thr Val Ser Ser
        115                 120


<210> SEQ ID NO 23
<211> LENGTH: 125
<212> TYPE: PRT
<213> ORGANISM: Gallus gallus

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ala Gly Ile Ser Tyr Ile Gly Arg Asn Glu Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Asn Leu Arg Ala Glu Asp Thr Ala Ile Tyr Tyr Cys
                85                  90                  95

Ala Lys His Leu Thr Gly Gly Thr Thr Asp Tyr Tyr Tyr Tyr Gly Met
            100                 105                 110

Asp Val Trp Gly Gln Gly Thr Thr Val Thr Val Ser Ser
        115                 120                 125


<210> SEQ ID NO 24
<211> LENGTH: 125
<212> TYPE: PRT
<213> ORGANISM: Gallus gallus

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Ser Gln Ala Pro Gly Lys Gly Leu Glu Trp Val
        35                  40                  45

Ala Gly Ile Ser Tyr Asp Gly Ser Ser Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys His Leu Thr Gly Gly Thr Thr Asp Tyr Tyr Tyr Tyr Ala Met
            100                 105                 110

Asp Val Trp Gly Gln Gly Thr Thr Val Thr Val Ser Ser
        115                 120                 125
```

<210> SEQ ID NO 25
<211> LENGTH: 120
<212> TYPE: PRT
<213> ORGANISM: Gallus gallus

<400> SEQUENCE: 25

```
Glu Val Gln Leu Leu Glu Ser Gly Gly Gly Trp Val Gln Pro Gly Gly
1               5                   10                  15

Ser Leu Arg Leu Ser Cys Ala Ala Ser Gly Phe Thr Phe Ile Asp Tyr
            20                  25                  30

Trp Met Ser Trp Val Arg Gln Ala Pro Gly Lys Gly Leu Glu Trp Val
        35                  40                  45

Ser Ser Ile Ser Trp Ile Gly Asp Thr Thr Phe Tyr Ala Asp Ser Val
    50                  55                  60

Lys Gly Arg Phe Thr Ile Ser Arg Asp Ser Ser Leu Asn Thr Val Tyr
65                  70                  75                  80

Leu Gln Met Asn Ser Leu Arg Ala Glu Asp Thr Ala Val Tyr Tyr Cys
                85                  90                  95

Ala Lys His Trp Thr Val Tyr Gln Tyr Gly Met Asp Val Trp Gly Gln
            100                 105                 110

Gly Thr Thr Val Thr Val Ser Ser
        115                 120
```

<210> SEQ ID NO 26
<211> LENGTH: 121
<212> TYPE: PRT
<213> ORGANISM: Gallus gallus

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Tyr Val
        35                  40                  45

Ala Ser Ile Asn Trp Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Asp Gln Asn Trp Asn Phe Tyr Tyr Gly Met Asp Val Trp Gly
            100                 105                 110

Gln Gly Thr Thr Val Thr Val Ser Ser
        115                 120
```

<210> SEQ ID NO 27
<211> LENGTH: 121
<212> TYPE: PRT
<213> ORGANISM: Gallus gallus

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Asn Trp Val Arg Gln Ala Pro Gly Lys Gly Leu Glu Tyr Val
        35                  40                  45

Ala Ser Ile Asn Trp Asn Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Asn Trp Asn Phe Tyr Tyr Gly Met Asp Val Trp Gly
            100                 105                 110

Gln Gly Thr Thr Val Thr Val Ser Ser
        115                 120


<210> SEQ ID NO 28
<211> LENGTH: 125
<212> TYPE: PRT
<213> ORGANISM: Gallus gallus

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Thr Ser Tyr
            20                  25                  30

Ala Met Ser Trp Val Ser Gln Ala Pro Gly Lys Gly Leu Glu Trp Val
        35                  40                  45

Ala Gly Ile Ser Tyr Asp Gly Ser Ile Lys Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys His Leu Thr Gly Gly Thr Thr Asp Tyr Tyr Tyr Tyr Ala Met
            100                 105                 110

Asp Val Trp Gly Gln Gly Thr Thr Val Thr Val Ser Ser
        115                 120                 125


<210> SEQ ID NO 29
<211> LENGTH: 118
<212> TYPE: PRT
<213> ORGANISM: Gallus gallus

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Trp Met Ser Trp Val Arg Gln Ala Pro Gly Lys Gly Leu Glu Trp Val
        35                  40                  45

Ser Thr Thr Ser Ser Ser Ser Trp Asn Asn Tyr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Ser Tyr Gly Met Asp Val Trp Gly Gln Gly Thr
            100                 105                 110
```

Thr Val Thr Val Ser Ser
        115

<210> SEQ ID NO 30
<211> LENGTH: 120
<212> TYPE: PRT
<213> ORGANISM: Gallus gallus

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Trp Ile Val Phe Gln Tyr Gly Leu Asp Ile Trp Gly Gln
            100                 105                 110

Gly Thr Thr Val Thr Val Ser Ser
        115                 120

<210> SEQ ID NO 31
<211> LENGTH: 119
<212> TYPE: PRT
<213> ORGANISM: Gallus gallus

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Tyr Ser Gly Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Glu Asn Trp Lys Glu Asn Asn Ala Met Asp Val Trp Gly Gln Gly
            100                 105                 110

Thr Thr Val Thr Val Ser Ser
        115

<210> SEQ ID NO 32
<211> LENGTH: 120
<212> TYPE: PRT
<213> ORGANISM: Gallus gallus

<400> SEQUENCE: 32

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Trp Ile Val Tyr Gln Tyr Gly Met Asp Val Trp Gly Gln
            100                 105                 110

Gly Thr Thr Val Thr Val Ser Ser
        115                 120


<210> SEQ ID NO 33
<211> LENGTH: 120
<212> TYPE: PRT
<213> ORGANISM: Gallus gallus

<400> SEQUENCE: 33

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Trp Ile Val Phe Gln Tyr Gly Leu Asp Val Trp Gly Gln
            100                 105                 110

Gly Thr Thr Val Thr Val Ser Ser
        115                 120


<210> SEQ ID NO 34
<211> LENGTH: 120
<212> TYPE: PRT
<213> ORGANISM: Gallus gallus

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg His Trp Ile Val Leu Gln Tyr Gly Leu Asp Val Trp Gly Gln
            100                 105                 110

Gly Thr Thr Val Thr Val Ser Ser
        115                 120


<210> SEQ ID NO 35
<211> LENGTH: 123
<212> TYPE: PRT
<213> ORGANISM: Gallus gallus

<400> SEQUENCE: 35

Val Glu Ser Gly Gly Gly Leu Val Gln Pro Gly Gly Ser Leu Arg Leu
1               5                   10                  15

Ser Cys Ala Ala Ser Gly Phe Thr Val Ser Asp His Tyr Val Ser Trp
            20                  25                  30

Val Arg Gln Ala Pro Gly Lys Gly Leu Glu Trp Val Ser Thr Ser Ser
        35                  40                  45

Ser Thr Asn Trp Asn Asp Gly Arg Thr Tyr Tyr Ala Asp Ser Val Lys
    50                  55                  60

Gly Arg Phe Thr Ile Ser Arg Asp Asn Ser Glu Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Gln Tyr Lys Gly Asn Asp Tyr Tyr Tyr Tyr Gly Met Asp Val
            100                 105                 110

Trp Gly Gln Gly Thr Thr Val Thr Val Ser Ser
        115                 120


<210> SEQ ID NO 36
<211> LENGTH: 120
<212> TYPE: PRT
<213> ORGANISM: Gallus gallus

<400> SEQUENCE: 36

Glu Val Gln Leu Leu Glu Leu Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Ser Trp Val Arg Gln Ala Pro Gly Lys Gly Leu Glu Trp Val
        35                  40                  45

Ser Leu Ile Asn Trp Asn Gly Asp Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Trp Ile Val Phe Gln Tyr Gly Leu Asp Val Trp Gly Gln
            100                 105                 110

Gly Thr Thr Val Thr Val Ser Ser
        115                 120


<210> SEQ ID NO 37
<211> LENGTH: 118
<212> TYPE: PRT
<213> ORGANISM: Gallus gallus
```

<400> SEQUENCE: 37

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Val Ser Ser Asn
20 25 30

Trp Met Ser Trp Val Arg Gln Ala Pro Gly Lys Gly Leu Glu Trp Val
35 40 45

Ser Thr Thr Ser Ser Ser Ser Trp Asn Asn Tyr Thr Tyr Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Lys Gly Ser Tyr Gly Met Asp Val Trp Gly Gln Gly Thr
100 105 110

Thr Val Thr Val Ser Ser
115

<210> SEQ ID NO 38
<211> LENGTH: 119
<212> TYPE: PRT
<213> ORGANISM: Gallus gallus

<400> SEQUENCE: 38

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Asn Trp Val Arg Gln Ala Pro Gly Lys Gly Leu Glu Trp Val
35 40 45

Ser Gly Ile Tyr Ser Gly Gly Thr Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Thr
85 90 95

Arg Glu Asn Trp Lys Glu Asn Asn Ala Met Asp Val Trp Gly Gln Gly
100 105 110

Thr Thr Val Thr Val Ser Ser
115

<210> SEQ ID NO 39
<211> LENGTH: 120
<212> TYPE: PRT
<213> ORGANISM: Gallus gallus

<400> SEQUENCE: 39

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asp Tyr
20 25 30

Val Met Ser Trp Val Arg Gln Ala Pro Gly Lys Gly Leu Glu Trp Val
35 40 45

Ser Leu Ile Asn Trp Ser Gly Gly Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Trp Ile Val Tyr Gln Tyr Gly Met Asp Val Trp Gly Gln
100 105 110

Gly Thr Thr Val Thr Val Ser Ser
115 120

<210> SEQ ID NO 40
<211> LENGTH: 119
<212> TYPE: PRT
<213> ORGANISM: Gallus gallus

<400> SEQUENCE: 40

Glu Val Gln Leu Leu Glu Ser Gly Gly Gly Leu Val Gln Pro Gly Gly
1 5 10 15

Ser Leu Arg Leu Ser Cys Ala Thr Ser Gly Phe Thr Val Ser Asp His
20 25 30

Tyr Val Ser Trp Val Arg Gln Ala Pro Gly Lys Gly Leu Glu Trp Val
35 40 45

Ser Thr Ser Ser Ser Thr Asn Trp Asn Asp Gly Arg Thr Tyr Tyr Ala
50 55 60

Asp Ser Val Lys Gly Arg Phe Thr Ile Ser Arg Asp Asn Ser Glu Asn
65 70 75 80

Thr Leu Tyr Leu Gln Met Asn Ser Leu Arg Ala Glu Asp Thr Ala Val
85 90 95

Tyr Tyr Cys Ala Lys Gly Ser Tyr Gly Met Asp Val Trp Gly Gln Gly
100 105 110

Thr Thr Val Thr Val Ser Ser
115

<210> SEQ ID NO 41
<211> LENGTH: 119
<212> TYPE: PRT
<213> ORGANISM: Gallus gallus

<400> SEQUENCE: 41

Glu Val Gln Leu Leu Glu Ser Gly Gly Gly Leu Val Gln Pro Gly Gly
1 5 10 15

Ser Leu Arg Leu Ser Cys Ala Thr Ser Gly Phe Thr Phe Ser Ser Tyr
20 25 30

Trp Met Ser Trp Val Arg Gln Ala Pro Gly Lys Gly Leu Glu Trp Val
35 40 45

Ser Gly Ile His Ile Ser Asp Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly His Thr Val Leu Gln Tyr Gly Met Asp Val Trp Gly Gln Gly
100 105 110

Thr Thr Val Thr Val Ser Ser
115

<210> SEQ ID NO 42
<211> LENGTH: 124

<212> TYPE: PRT
<213> ORGANISM: Gallus gallus

<400> SEQUENCE: 42

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Phe
20 25 30

Trp Met Ser Trp Val Arg Gln Ala Pro Gly Lys Gly Leu Glu Trp Val
35 40 45

Ser Ser Ile Ile Asn Ile Gln Thr Tyr Asp Tyr Ala Thr Tyr Tyr Ala
50 55 60

Asp Ser Val Lys Gly Arg Phe Thr Ile Ser Arg Asp Asn Ser Lys Asn
65 70 75 80

Thr Leu Tyr Leu Gln Met Asn Ser Leu Arg Ala Glu Asp Thr Ala Ile
85 90 95

Tyr Tyr Cys Ala Lys Asp Val Ala Pro Gly Leu Pro Gly Gly Met Asp
100 105 110

Val Trp Gly Gln Gly Thr Thr Val Thr Val Ser Ser
115 120

<210> SEQ ID NO 43
<211> LENGTH: 124
<212> TYPE: PRT
<213> ORGANISM: Gallus gallus

<400> SEQUENCE: 43

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Phe
20 25 30

Trp Met Ser Trp Val Arg Gln Ala Pro Gly Lys Gly Leu Glu Trp Val
35 40 45

Ser Ser Ile Ile Asn Ile Gln Thr Tyr Asp Tyr Ala Thr Tyr Tyr Ala
50 55 60

Asp Ser Val Lys Gly Arg Phe Thr Ile Ser Arg Asp Asn Ser Lys Asn
65 70 75 80

Thr Leu Tyr Leu Gln Met Asn Ser Leu Arg Ala Glu Asp Thr Ala Ile
85 90 95

Tyr Tyr Cys Ala Lys Asp Val Ala Pro Gly Leu Pro Gly Gly Met Asp
100 105 110

Val Trp Gly Gln Gly Thr Thr Val Thr Val Ser Ser
115 120

<210> SEQ ID NO 44
<211> LENGTH: 119
<212> TYPE: PRT
<213> ORGANISM: Gallus gallus

<400> SEQUENCE: 44

Glu Val Gln Leu Leu Glu Ser Gly Gly Gly Leu Val Gln Pro Gly Gly
1 5 10 15

Ser Leu Arg Pro Ser Cys Ala Thr Ser Gly Phe Thr Phe Ser Ser Tyr
20 25 30

Trp Met Ser Trp Val Arg Gln Ala Pro Gly Lys Gly Leu Glu Trp Val
35 40 45

Ser Gly Ile His Ile Ser Asp Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly His Thr Val Leu Gln Tyr Gly Met Asp Val Trp Gly Gln Gly
100 105 110

Thr Thr Val Thr Val Ser Ser
115

<210> SEQ ID NO 45
<211> LENGTH: 120
<212> TYPE: PRT
<213> ORGANISM: Gallus gallus

<400> SEQUENCE: 45

Glu Val Gln Leu Leu Glu Ser Gly Gly Asp Leu Val Gln Ser Gly Gly
1 5 10 15

Ser Leu Arg Leu Ser Cys Ala Ala Ser Gly Phe Ser Phe Trp Gly Tyr
20 25 30

Ala Met Thr Trp Val Arg Gln Ala Pro Gly Lys Gly Leu Glu Trp Val
35 40 45

Ser Thr Ile Ala Gly Asn Ser Tyr Thr Tyr Tyr Ala Asp Ser Val Lys
50 55 60

Gly Arg Phe Thr Ile Ser Arg Asp Asn Ser Lys Asn Met Val Tyr Leu
65 70 75 80

Gln Met Asn Gly Leu Arg Ala Glu Asp Thr Ala Val Tyr Tyr Cys Ala
85 90 95

Lys Asp Arg Ser Phe Tyr Asn Tyr Tyr Asp Ile Asp Val Trp Gly Gln
100 105 110

Gly Thr Thr Val Thr Val Ser Ser
115 120

<210> SEQ ID NO 46
<211> LENGTH: 119
<212> TYPE: PRT
<213> ORGANISM: Gallus gallus

<400> SEQUENCE: 46

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ser Gly Ile His Ile Ser Asp Ser Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly His Thr Val Leu Gln Tyr Gly Met Asp Val Trp Gly Gln Gly
100 105 110

Thr Thr Val Thr Val Ser Ser
115

<210> SEQ ID NO 47
<211> LENGTH: 122
<212> TYPE: PRT
<213> ORGANISM: Gallus gallus

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ser Met Ser Trp Val Arg Gln Ala Pro Gly Lys Gly Leu Glu Trp Val
        35                  40                  45

Ser Thr Ile Asn Ser Gly Ser Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Cys Asn Gly Tyr His Cys Tyr Gly Met Asp Val Trp
            100                 105                 110

Gly Leu Gly Thr Thr Val Thr Val Ser Ser
        115                 120
```

<210> SEQ ID NO 48
<211> LENGTH: 120
<212> TYPE: PRT
<213> ORGANISM: Gallus gallus

<400> SEQUENCE: 48

```
Glu Val Gln Leu Leu Glu Ser Gly Gly Asp Leu Val Gln Ser Gly Gly
1               5                   10                  15

Ser Leu Arg Leu Ser Cys Ala Ala Ser Gly Phe Ser Phe Trp Gly Tyr
            20                  25                  30

Ala Met Thr Trp Val Arg Gln Ala Pro Gly Lys Gly Leu Glu Trp Val
        35                  40                  45

Ser Thr Ile Ala Gly Asn Ser Tyr Ala Tyr Tyr Ala Asp Ser Val Lys
    50                  55                  60

Gly Arg Phe Thr Ile Ser Arg Asp Asn Ser Lys Asn Met Val Tyr Leu
65                  70                  75                  80

Gln Met Asn Gly Leu Arg Ala Glu Asp Thr Ala Val Tyr Tyr Cys Ala
                85                  90                  95

Lys Asp Arg Ser Phe Tyr Asn Tyr Tyr Asp Ile Asp Val Trp Gly Gln
            100                 105                 110

Gly Thr Thr Val Thr Val Ser Ser
        115                 120
```

<210> SEQ ID NO 49
<211> LENGTH: 119
<212> TYPE: PRT
<213> ORGANISM: Gallus gallus

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Ala Ile Tyr Phe Asp Gly Ser Ile Tyr Asp Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Asp Glu Asp Thr Ala Val Tyr Tyr Cys Ala
                85                  90                  95

Lys Ser His Thr Val Leu Gln Tyr Gly Met Asp Val Trp Gly Gln Gly
            100                 105                 110

Thr Thr Val Thr Val Ser Ser
        115


<210> SEQ ID NO 50
<211> LENGTH: 124
<212> TYPE: PRT
<213> ORGANISM: Gallus gallus

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Trp Met Ser Trp Val Arg Gln Ala Pro Gly Lys Gly Leu Glu Trp Val
        35                  40                  45

Ser Ser Ile Ile Asn Ile Gln Thr Tyr Asp Tyr Ala Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Ile
                85                  90                  95

Tyr Tyr Cys Ala Lys Asp Val Ala Pro Gly Leu Pro Gly Gly Met Asp
            100                 105                 110

Val Trp Gly Gln Gly Thr Thr Val Thr Val Ser Ser
        115                 120


<210> SEQ ID NO 51
<211> LENGTH: 119
<212> TYPE: PRT
<213> ORGANISM: Gallus gallus

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile His Ile Ser Asp Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly His Thr Val Leu Gln Tyr Gly Met Asp Val Trp Gly Gln Gly
            100                 105                 110
```

Thr Thr Val Thr Val Ser Ser
115

<210> SEQ ID NO 52
<211> LENGTH: 121
<212> TYPE: PRT
<213> ORGANISM: Gallus gallus

<400> SEQUENCE: 52

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Trp Met Ser Trp Val Arg Gln Ala Pro Gly Lys Gly Leu Glu Trp Val
35 40 45

Ser Ser Ile Asn Trp Asn Gly Asp Asn Thr Tyr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Met Asn Ser Leu Arg Ala Glu Asp Thr Ala Val Tyr Tyr
85 90 95

Cys Ala Lys Ser His Thr Val Leu Gln Tyr Gly Met Asp Val Trp Gly
100 105 110

Gln Gly Thr Thr Val Thr Val Ser Ser
115 120

<210> SEQ ID NO 53
<211> LENGTH: 121
<212> TYPE: PRT
<213> ORGANISM: Gallus gallus

<400> SEQUENCE: 53

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Tyr Met Ser Trp Val Arg Gln Ala Pro Gly Lys Gly Leu Glu Trp Val
35 40 45

Ser Ala Ile Ser Ile Phe Ser Gly Asp Ser Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Met Asn Ser Leu Arg Ala Glu Asp Thr Ala Val Tyr Tyr
85 90 95

Cys Ala Lys Ser His Thr Val Leu Gln Tyr Gly Met Asp Val Trp Gly
100 105 110

Gln Gly Thr Thr Val Thr Val Ser Ser
115 120

<210> SEQ ID NO 54
<211> LENGTH: 120
<212> TYPE: PRT
<213> ORGANISM: Gallus gallus

<400> SEQUENCE: 54

Glu Val Gln Leu Leu Glu Ser Gly Gly Gly Leu Val Gln Ala Gly Gly
1 5 10 15

```
Ser Leu Arg Leu Ser Cys Ala Ala Ser Gly Phe Thr Phe Asp Asp Tyr
            20                  25                  30

Val Met Thr Trp Val Arg Gln Ala Pro Gly Lys Gly Leu Glu Trp Val
        35                  40                  45

Ser Leu Ile Asn Trp Ser Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys His Asn Leu Asn Tyr Tyr Tyr Gly Met Asp Val Trp Gly Gln
            100                 105                 110

Gly Thr Thr Val Thr Val Ser Ser
        115                 120


<210> SEQ ID NO 55
<211> LENGTH: 110
<212> TYPE: PRT
<213> ORGANISM: Gallus gallus

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Ser Gly Ile Ser Ala Lys Ile Gly Asn Asn
            20                  25                  30

Tyr Val Ser Trp Tyr Gln Gln Leu Pro Gly Thr Ala Pro Lys Leu Leu
        35                  40                  45

Ile Tyr Phe Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Ala Trp Leu Phe Gly Gly Gly Thr Lys Leu Thr Val Leu
            100                 105                 110


<210> SEQ ID NO 56
<211> LENGTH: 110
<212> TYPE: PRT
<213> ORGANISM: Gallus gallus

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ile Ser Ala Lys Ile Gly Asn Asn
            20                  25                  30

Tyr Val Ser Trp Tyr Gln Gln Leu Pro Gly Thr Ala Pro Lys Leu Leu
        35                  40                  45

Ile Tyr Phe Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Ala Trp Leu Phe Gly Gly Gly Thr Lys Leu Thr Val Leu
            100                 105                 110
```

<210> SEQ ID NO 57
<211> LENGTH: 110
<212> TYPE: PRT
<213> ORGANISM: Gallus gallus

<400> SEQUENCE: 57

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Leu Gly Asn Asn
            20                  25                  30

Leu Val Tyr Trp Tyr Gln Gln Leu Pro Gly Thr Ala Pro Lys Leu Leu
        35                  40                  45

Ile Tyr Phe Asn Asn Glu Arg Pro Ser Gly Val Pro Asp Arg Phe Ser
    50                  55                  60

Gly Ser Lys Ser Gly Thr Ser Ala Ser Leu Ala Ile Ser Gly Val Gln
65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
            100                 105                 110
```

<210> SEQ ID NO 58
<211> LENGTH: 111
<212> TYPE: PRT
<213> ORGANISM: Gallus gallus

<400> SEQUENCE: 58

```
Gln Ser Val Met Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Arg Tyr Val His Trp Tyr Lys Gln Val Pro Gly Thr Ala Pro Lys Leu
        35                  40                  45

Leu Ile Tyr Gly Asn His Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Gly Ser
                85                  90                  95

Leu Ser Gly Trp Val Phe Gly Gly Gly Thr Lys Leu Thr Val Leu
            100                 105                 110
```

<210> SEQ ID NO 59
<211> LENGTH: 110
<212> TYPE: PRT
<213> ORGANISM: Gallus gallus

<400> SEQUENCE: 59

```
Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Thr Asn
            20                  25                  30

Tyr Val Ser Trp Tyr Gln Gln Leu Pro Gly Thr Ala Pro Lys Leu Leu
        35                  40                  45

Leu Tyr Lys Glu Asp Gln Arg Pro Ser Gly Val Pro Asp Arg Phe Ser
    50                  55                  60
```

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Thr Trp Asp Gly Ser Leu
85 90 95

Arg Ser Trp Val Phe Gly Gly Gly Thr Lys Leu Thr Val Leu
100 105 110

<210> SEQ ID NO 60
<211> LENGTH: 111
<212> TYPE: PRT
<213> ORGANISM: Gallus gallus

<400> SEQUENCE: 60

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Ser
20 25 30

Arg Tyr Val His Trp Tyr Gln His Leu Pro Gly Thr Ala Pro Lys Leu
35 40 45

Leu Ile Tyr Leu Asp Ser Gln Arg Pro Ser Gly Val Pro Asp Arg Phe
50 55 60

Ser Ala Ser Lys Ser Gly Thr Ser Ala Ser Leu Ala Ile Ser Gly Leu
65 70 75 80

Gln Ser Glu Asp Glu Ala Asp Tyr Tyr Cys Ser Ala Trp Asp Asp Ser
85 90 95

Leu Ser Ala Trp Val Phe Gly Gly Gly Thr Lys Leu Thr Val Leu
100 105 110

<210> SEQ ID NO 61
<211> LENGTH: 110
<212> TYPE: PRT
<213> ORGANISM: Gallus gallus

<400> SEQUENCE: 61

Gln Ser Val Leu Thr Gln Pro Pro Ser Ala Ser Gly Thr Pro Gly Gln
1 5 10 15

Arg Val Ile Ile Ser Cys Ser Gly Ser Thr Ser Asp Ile Glu Thr Lys
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ala Trp Asp Asn Thr Leu
85 90 95

Lys Ser Trp Val Phe Gly Gly Gly Thr Lys Leu Thr Val Leu
100 105 110

<210> SEQ ID NO 62
<211> LENGTH: 110
<212> TYPE: PRT
<213> ORGANISM: Gallus gallus

<400> SEQUENCE: 62

Gln Ser Val Leu Thr Gln Pro Pro Ser Ala Ser Gly Thr Pro Gly Gln
1 5 10 15

Arg Val Thr Ile Ser Cys Ser Gly Ser Arg Ser Asn Val Gly Asp His
20 25 30

Tyr Val Ser Trp Tyr Gln Gln Phe Pro Gly Thr Ala Pro Lys Leu Leu
35 40 45

Ile Tyr Ala Asn Tyr Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp His Tyr Cys Ala Ser Trp Asp Ala Ser Leu
85 90 95

Asn Val Trp Val Phe Gly Gly Gly Thr Lys Leu Thr Val Leu
100 105 110

<210> SEQ ID NO 63
<211> LENGTH: 110
<212> TYPE: PRT
<213> ORGANISM: Gallus gallus

<400> SEQUENCE: 63

Gln Ser Val Leu Thr Gln Pro Pro Ser Ala Ser Gly Thr Pro Gly Gln
1 5 10 15

Arg Val Thr Ile Ser Cys Ser Gly Ser Ile Ser Asn Ile Glu Thr Lys
20 25 30

Tyr Val Ser Trp Tyr Gln Gln Leu Pro Gly Thr Ala Pro Lys Leu Leu
35 40 45

Ile Tyr Asn Ser Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Val Ser Trp Asp Ala Ser Leu
85 90 95

Lys Ser Trp Val Phe Gly Gly Gly Thr Lys Leu Thr Val Leu
100 105 110

<210> SEQ ID NO 64
<211> LENGTH: 110
<212> TYPE: PRT
<213> ORGANISM: Gallus gallus

<400> SEQUENCE: 64

Gln Ser Val Leu Thr Gln Pro Ala Ser Ala Ser Gly Thr Pro Gly Gln
1 5 10 15

Arg Val Thr Ile Thr Cys Ser Gly Thr Ile Ser Asn Ile Glu Thr Lys
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ser Trp Glu Asn Asp Leu
85 90 95

Lys Ser Trp Val Phe Gly Gly Gly Thr Lys Leu Thr Val Leu
100 105 110

<210> SEQ ID NO 65

<211> LENGTH: 110
<212> TYPE: PRT
<213> ORGANISM: Gallus gallus

<400> SEQUENCE: 65

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Phe Asn Ile Gly Thr Lys
            20                  25                  30

Tyr Leu Tyr Trp Tyr Gln Gln Leu Pro Gly Thr Ala Pro Lys Leu Leu
        35                  40                  45

Ile Tyr Leu Asp Ser Gln Arg Pro Ser Gly Val Pro Asp Arg Phe Ser
    50                  55                  60

Thr Ser Lys Pro Gly Thr Ser Ala Ser Leu Ala Ile Ser Gly Leu Gln
65                  70                  75                  80

Ser Glu Asp Glu Ala Asp Tyr Tyr Cys Ala Leu Trp Asp Asp His Leu
                85                  90                  95

His Gly Trp Val Phe Gly Gly Gly Thr Lys Leu Thr Val Leu
            100                 105                 110
```

<210> SEQ ID NO 66
<211> LENGTH: 110
<212> TYPE: PRT
<213> ORGANISM: Gallus gallus

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Glu Thr Lys
            20                  25                  30

Tyr Val Ser Trp Tyr Gln Gln Leu Pro Gly Thr Ala Pro Lys Leu Leu
        35                  40                  45

Ile Tyr Asn Ser Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Val Ser Trp Asp Ala Ser Leu
                85                  90                  95

Lys Ser Trp Val Phe Gly Gly Gly Thr Lys Leu Thr Val Leu
            100                 105                 110
```

<210> SEQ ID NO 67
<211> LENGTH: 110
<212> TYPE: PRT
<213> ORGANISM: Gallus gallus

<400> SEQUENCE: 67

```
Gln Ser Val Leu Thr Gln Pro Pro Ser Ala Ser Gly Thr Pro Gly Gln
1               5                   10                  15

Arg Val Thr Ile Ser Cys Ser Gly Ser Ile Ser Asn Ile Glu Thr Lys
            20                  25                  30

Tyr Val Ser Trp Tyr Gln Gln Leu Pro Gly Thr Ala Pro Lys Leu Leu
        35                  40                  45

Ile Tyr Asn Ser Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Val Ser Trp Asp Ala Ser Leu
                85                  90                  95

Lys Ser Trp Val Phe Gly Gly Gly Thr Lys Leu Thr Val Leu
            100                 105                 110


<210> SEQ ID NO 68
<211> LENGTH: 110
<212> TYPE: PRT
<213> ORGANISM: Gallus gallus

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Thr Ile Ser Asn Ile Glu Ile Lys
            20                  25                  30

Tyr Val Ser Trp Tyr Gln Gln Leu Pro Gly Thr Ala Pro Lys Leu Leu
        35                  40                  45

Ile Tyr Gly Asn His Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Trp Glu Asn Asp Leu
                85                  90                  95

Lys Ser Trp Val Phe Gly Gly Gly Thr Lys Leu Thr Val Leu
            100                 105                 110


<210> SEQ ID NO 69
<211> LENGTH: 110
<212> TYPE: PRT
<213> ORGANISM: Gallus gallus

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Thr Ile Ser Asn Ile Glu Ile Lys
            20                  25                  30

Tyr Val Ser Trp Tyr Gln Gln Leu Pro Gly Thr Ala Pro Lys Leu Leu
        35                  40                  45

Ile Tyr Gly Asn His Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Trp Glu Asn Asp Leu
                85                  90                  95

Lys Ser Trp Val Phe Gly Gly Gly Thr Lys Leu Thr Val Leu
            100                 105                 110


<210> SEQ ID NO 70
<211> LENGTH: 110
<212> TYPE: PRT
<213> ORGANISM: Gallus gallus

<400> SEQUENCE: 70

Gln Ser Val Leu Thr Gln Pro Ala Ser Ala Ser Gly Thr Pro Gly Gln
1               5                   10                  15

Arg Val Thr Ile Ser Cys Ser Gly Thr Ile Ser Asn Ile Glu Thr Lys
            20                  25                  30
```

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ser Trp Glu Asn Asp Leu
85 90 95

Lys Ser Trp Val Phe Gly Gly Gly Thr Lys Leu Thr Val Leu
100 105 110

<210> SEQ ID NO 71
<211> LENGTH: 110
<212> TYPE: PRT
<213> ORGANISM: Gallus gallus

<400> SEQUENCE: 71

Gln Ser Val Leu Thr Gln Pro Pro Ser Ala Ser Gly Thr Pro Gly Gln
1 5 10 15

Arg Val Thr Ile Ser Cys Ser Gly Thr Ile Ser Asn Ile Glu Ile Lys
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ser Ser Trp Glu Asn Asp Leu
85 90 95

Lys Ser Trp Val Phe Gly Gly Gly Thr Lys Leu Thr Val Leu
100 105 110

<210> SEQ ID NO 72
<211> LENGTH: 110
<212> TYPE: PRT
<213> ORGANISM: Gallus gallus

<400> SEQUENCE: 72

Gln Ser Val Leu Thr Gln Pro Pro Ser Ala Ser Gly Thr Pro Gly Gln
1 5 10 15

Arg Val Thr Ile Ser Cys Ser Gly Ser Asn Phe Asn Ile Gly Thr Lys
20 25 30

Tyr Leu Tyr Trp Tyr Gln Gln Leu Pro Gly Thr Ala Pro Lys Leu Leu
35 40 45

Ile Tyr Leu Asp Ser Gln Arg Pro Ser Gly Val Pro Asp Arg Phe Ser
50 55 60

Thr Ser Lys Ser Gly Thr Ser Ala Ser Leu Ala Ile Ser Gly Leu Gln
65 70 75 80

Ser Glu Asp Glu Ala Asp Tyr Tyr Cys Ala Leu Trp Asp Asp His Leu
85 90 95

His Gly Trp Val Phe Gly Gly Gly Thr Lys Leu Thr Val Leu
100 105 110

<210> SEQ ID NO 73
<211> LENGTH: 110
<212> TYPE: PRT
<213> ORGANISM: Gallus gallus

<400> SEQUENCE: 73

Gln Ser Val Leu Thr Gln Pro Ala Ser Ala Ser Gly Thr Pro Gly Gln
1 5 10 15

Arg Val Thr Ile Ser Cys Ser Gly Thr Ile Ser Asn Ile Glu Thr Lys
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ser Trp Glu Asn Asp Leu
85 90 95

Lys Ser Trp Val Phe Gly Gly Gly Thr Lys Leu Thr Val Leu
100 105 110

<210> SEQ ID NO 74
<211> LENGTH: 110
<212> TYPE: PRT
<213> ORGANISM: Gallus gallus

<400> SEQUENCE: 74

Gln Ser Val Leu Thr Gln Pro Pro Ser Ala Ser Gly Thr Pro Gly Gln
1 5 10 15

Arg Val Thr Ile Ser Cys Ser Gly Ser Ile Ser Asn Ile Glu Thr Lys
20 25 30

Tyr Val Ser Trp Tyr Gln Gln Leu Pro Gly Thr Ala Pro Lys Leu Leu
35 40 45

Ile Tyr Asn Ser Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Val Ser Trp Asp Ala Ser Leu
85 90 95

Lys Ser Trp Val Phe Gly Gly Gly Thr Lys Leu Thr Val Leu
100 105 110

<210> SEQ ID NO 75
<211> LENGTH: 110
<212> TYPE: PRT
<213> ORGANISM: Gallus gallus

<400> SEQUENCE: 75

Gln Ser Val Leu Thr Gln Pro Leu Ser Ala Ser Gly Thr Pro Gly Gln
1 5 10 15

Arg Val Thr Ile Ser Cys Ser Gly Val Ser Ser Asn Ile Glu Ile Lys
20 25 30

Tyr Val Ser Trp Tyr Gln Gln Leu Pro Gly Thr Ala Pro Lys Leu Leu
35 40 45

Ile Tyr Asn Ser His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Asp Arg Leu
85 90 95

Lys Ser Trp Val Phe Gly Gly Gly Thr Lys Leu Thr Val Leu
100 105 110

<210> SEQ ID NO 76
<211> LENGTH: 110
<212> TYPE: PRT
<213> ORGANISM: Gallus gallus

<400> SEQUENCE: 76

Gln Ser Val Leu Thr Gln Pro Pro Ser Ala Ser Gly Thr Pro Gly Gln
1 5 10 15

Arg Val Thr Ile Ser Cys Ser Gly Ser Ile Ser Asn Ile Glu Thr Lys
20 25 30

Tyr Val Ser Trp Tyr Gln Gln Leu Pro Gly Thr Ala Pro Lys Leu Leu
35 40 45

Ile Tyr Asn Ser Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Val Ser Trp Asp Ala Ser Leu
85 90 95

Lys Ser Trp Val Phe Gly Gly Gly Thr Lys Leu Thr Val Leu
100 105 110

<210> SEQ ID NO 77
<211> LENGTH: 111
<212> TYPE: PRT
<213> ORGANISM: Gallus gallus

<400> SEQUENCE: 77

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Ser
20 25 30

Arg Tyr Val His Trp Tyr Gln Gln Leu Pro Gly Thr Ala Pro Lys Leu
35 40 45

Leu Ile Tyr Phe Asp Ser Gln Arg Pro Ser Gly Val Pro Asp Arg Phe
50 55 60

Ser Ala Ser Lys Ser Gly Thr Ser Ala Ser Leu Ala Ile Ser Gly Leu
65 70 75 80

Gln Ser Glu Asp Glu Ala Asp Tyr Tyr Cys Ala Thr Trp Asp Asp Ser
85 90 95

Leu Ser Ala Trp Val Phe Gly Gly Gly Thr Lys Leu Thr Val Leu
100 105 110

<210> SEQ ID NO 78
<211> LENGTH: 111
<212> TYPE: PRT
<213> ORGANISM: Gallus gallus

<400> SEQUENCE: 78

Gln Ser Val Leu Thr Gln Pro Pro Ser Ala Ser Gly Thr Pro Gly Gln
1 5 10 15

Arg Val Thr Ile Ser Cys Ser Gly Ser Arg Ser Asn Ile Gly Thr Asn
20 25 30

Arg Tyr Val His Trp Tyr Gln Gln Leu Pro Gly Thr Ala Pro Lys Leu
35 40 45

```
Leu Ile Tyr Gly Asn His Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Ser Ala Trp Val Phe Gly Gly Gly Thr Lys Leu Thr Val Leu
            100                 105                 110


<210> SEQ ID NO 79
<211> LENGTH: 110
<212> TYPE: PRT
<213> ORGANISM: Gallus gallus

<400> SEQUENCE: 79

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Lys Ile Gly Ser Lys
            20                  25                  30

Tyr Val His Trp Tyr Gln Gln Leu Pro Gly Thr Ala Pro Lys Leu Leu
        35                  40                  45

Ile Tyr Lys Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Arg Val
                85                  90                  95

Asn Ala Trp Val Phe Gly Gly Gly Thr Lys Leu Thr Val Leu
            100                 105                 110


<210> SEQ ID NO 80
<211> LENGTH: 110
<212> TYPE: PRT
<213> ORGANISM: Gallus gallus

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Asn Asn
            20                  25                  30

Phe Val Ser Trp Tyr Gln Gln Leu Pro Gly Thr Ala Pro Lys Leu Leu
        35                  40                  45

Ile Tyr Asn Glu Ile Lys Arg Pro Ser Gly Val Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Gly Ser Leu
                85                  90                  95

Arg Gly Trp Val Phe Gly Gly Gly Thr Lys Leu Thr Val Leu
            100                 105                 110


<210> SEQ ID NO 81
<211> LENGTH: 110
<212> TYPE: PRT
<213> ORGANISM: Gallus gallus
```

<400> SEQUENCE: 81

Gln Ser Val Leu Thr Gln Pro Pro Ser Ala Ser Gly Thr Pro Gly Gln
1 5 10 15

Arg Val Thr Ile Ser Cys Ser Gly Gly Ser Ser Asn Ile Gly Asn Asn
20 25 30

Phe Val Ser Trp Tyr Gln Gln Leu Pro Gly Thr Ala Pro Lys Leu Leu
35 40 45

Ile Tyr Asn Glu Ile Lys Arg Pro Ser Gly Val Pro Asp Arg Phe Ser
50 55 60

Ala Ser Lys Ser Gly Thr Ser Ala Ser Leu Ala Ile Ser Gly Leu Gln
65 70 75 80

Ser Glu Asp Glu Ala Asp Tyr Tyr Cys Ala Ser Trp Asp Gly Ser Leu
85 90 95

Arg Gly Trp Val Phe Gly Gly Gly Thr Lys Leu Thr Val Leu
100 105 110

<210> SEQ ID NO 82
<211> LENGTH: 111
<212> TYPE: PRT
<213> ORGANISM: Gallus gallus

<400> SEQUENCE: 82

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Asn
20 25 30

Arg Tyr Val His Trp Tyr Gln Gln Phe Pro Gly Thr Ala Pro Lys Leu
35 40 45

Leu Ile Tyr Gly Thr Asp Arg Arg Pro Ser Gly Val Ser Asp Arg Phe
50 55 60

Ser Gly Ser Lys Ser Gly Thr Ser Ala Ser Leu Ala Ile Ser Gly Leu
65 70 75 80

Gln Ser Glu Asp Glu Ala Asp Tyr Tyr Cys Ala Ala Trp Asp Asp Ser
85 90 95

Leu Ser Ala Trp Val Phe Gly Gly Gly Thr Lys Leu Thr Val Leu
100 105 110

<210> SEQ ID NO 83
<211> LENGTH: 110
<212> TYPE: PRT
<213> ORGANISM: Gallus gallus

<400> SEQUENCE: 83

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Gly Ala Lys
20 25 30

Tyr Leu Tyr Trp Tyr Gln Gln Leu Pro Gly Thr Ala Pro Lys Leu Leu
35 40 45

Ile Tyr Leu Asn Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Phe Trp Asp Asp His Leu
85 90 95

Lys Gly Trp Val Phe Gly Gly Gly Thr Lys Leu Thr Val Leu
100 105 110

<210> SEQ ID NO 84
<211> LENGTH: 110
<212> TYPE: PRT
<213> ORGANISM: Gallus gallus

<400> SEQUENCE: 84

Gln Ser Val Leu Thr Gln Pro Leu Ser Ala Ser Gly Thr Pro Gly Gln
1 5 10 15

Arg Val Thr Ile Ser Cys Ser Gly Val Ser Ser Asn Ile Glu Ile Lys
20 25 30

Tyr Val Ser Trp Tyr Gln Gln Leu Pro Gly Thr Ala Pro Lys Leu Leu
35 40 45

Ile Tyr Asn Ser His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Asp Arg Leu
85 90 95

Lys Ser Trp Val Phe Gly Gly Gly Thr Lys Leu Thr Val Leu
100 105 110

<210> SEQ ID NO 85
<211> LENGTH: 110
<212> TYPE: PRT
<213> ORGANISM: Gallus gallus

<400> SEQUENCE: 85

Gln Ser Val Leu Thr Gln Pro Pro Ser Ala Ser Gly Thr Pro Gly Gln
1 5 10 15

Arg Val Thr Ile Ser Cys Ser Gly Val Thr Ser Asn Ile Ala Ser Tyr
20 25 30

His Val Tyr Trp Tyr Gln Gln Leu Pro Gly Thr Ala Pro Lys Leu Leu
35 40 45

Ile Tyr Leu Asn Ser Gln Arg Pro Ser Gly Val Pro Asp Arg Phe Ser
50 55 60

Ala Ser Lys Ser Gly Thr Ser Ala Ser Leu Ala Ile Ser Gly Leu Gln
65 70 75 80

Ser Glu Asp Glu Ala Asp Tyr Tyr Cys Ala Thr Trp Asp Gly Ser Leu
85 90 95

Asn Gly Trp Val Phe Gly Gly Gly Thr Lys Leu Thr Val Leu
100 105 110

<210> SEQ ID NO 86
<211> LENGTH: 116
<212> TYPE: PRT
<213> ORGANISM: Gallus gallus

<400> SEQUENCE: 86

Gln Ser Val Leu Thr Gln Pro Ser Ser Ala Ser Gly Thr Pro Gly Gln
1 5 10 15

Arg Val Ala Ile Ser Cys Ser Gly Thr Ile Ser Asn Ile Glu Thr Lys
20 25 30

Tyr Val Ser Trp Tyr Lys Tyr Val Ser Trp Tyr Gln Gln Leu Pro Gly
35 40 45

Thr Ala Pro Lys Leu Leu Ile Tyr Asn Asn Val Gln Arg Pro Ser Gly
50 55 60

Val Pro Asp Arg Phe Ser Gly Ser Gln Ser Gly Thr Ser Ala Ser Leu
65 70 75 80

Ala Ile Ser Gly Leu Gln Ser Glu Asp Glu Ala His Tyr Tyr Cys Ala
85 90 95

Ser Trp Glu Gly Gly Leu Asn Ser Trp Val Phe Gly Gly Gly Thr Lys
100 105 110

Leu Thr Val Leu
115

<210> SEQ ID NO 87
<211> LENGTH: 110
<212> TYPE: PRT
<213> ORGANISM: Gallus gallus

<400> SEQUENCE: 87

Gln Ser Val Leu Thr Gln Pro Leu Ser Ala Ser Gly Thr Pro Gly Gln
1 5 10 15

Arg Val Thr Ile Ser Cys Ser Gly Val Ser Ser Asn Ile Glu Ile Lys
20 25 30

Tyr Val Ser Trp Tyr Gln Gln Leu Pro Gly Thr Ala Pro Lys Leu Leu
35 40 45

Ile Tyr Asn Ser His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Asp Arg Leu
85 90 95

Lys Ser Trp Val Phe Gly Gly Gly Thr Lys Leu Thr Val Leu
100 105 110

<210> SEQ ID NO 88
<211> LENGTH: 110
<212> TYPE: PRT
<213> ORGANISM: Gallus gallus

<400> SEQUENCE: 88

Gln Ser Val Leu Thr Gln Pro Leu Ser Ala Ser Gly Thr Pro Gly Gln
1 5 10 15

Arg Val Thr Ile Ser Cys Ser Gly Val Ser Ser Asn Ile Glu Ile Lys
20 25 30

Tyr Val Ser Trp Tyr Gln Gln Leu Pro Gly Thr Ala Pro Lys Leu Leu
35 40 45

Ile Tyr Asn Ser His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Asp Arg Leu
85 90 95

Lys Ser Trp Val Phe Gly Gly Gly Thr Lys Leu Thr Val Leu
100 105 110

<210> SEQ ID NO 89
<211> LENGTH: 110
<212> TYPE: PRT
<213> ORGANISM: Gallus gallus

<400> SEQUENCE: 89

Gln Ser Val Leu Thr Gln Pro Pro Ser Ala Ser Gly Thr Pro Gly Gln
1 5 10 15

Arg Val Thr Ile Ser Cys Ser Ala Ser Asn Ser Tyr Ile Gly Thr Lys
20 25 30

Tyr Phe Tyr Trp Tyr Gln Gln Leu Pro Gly Thr Ala Pro Lys Leu Leu
35 40 45

Ile Tyr Leu Asp Ser Gln Arg Pro Ser Gly Val Pro Asp Arg Phe Ser
50 55 60

Gly Ser Lys Ser Gly Thr Ser Val Ser Leu Ala Ile Ser Gly Leu Gln
65 70 75 80

Ser Glu Asp Glu Ala Asp Tyr Tyr Cys Ala Phe Trp Asp Asp His Leu
85 90 95

His Gly Trp Val Phe Gly Gly Gly Thr Lys Leu Thr Val Leu
100 105 110

<210> SEQ ID NO 90
<211> LENGTH: 110
<212> TYPE: PRT
<213> ORGANISM: Gallus gallus

<400> SEQUENCE: 90

Gln Ser Val Leu Thr Gln Pro Leu Ser Ala Ser Gly Thr Pro Gly Gln
1 5 10 15

Lys Val Thr Ile Ser Cys Ser Gly Val Ser Ser Asn Ile Glu Ile Lys
20 25 30

Tyr Val Ser Trp Tyr Gln Gln Leu Pro Gly Thr Ala Pro Lys Leu Leu
35 40 45

Ile Tyr Asn Ser His Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Asp Arg Leu
85 90 95

Lys Ser Trp Val Phe Gly Gly Gly Thr Lys Leu Thr Val Leu
100 105 110

<210> SEQ ID NO 91
<211> LENGTH: 110
<212> TYPE: PRT
<213> ORGANISM: Gallus gallus

<400> SEQUENCE: 91

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Gly Ala Lys
20 25 30

Tyr Leu Tyr Trp Tyr Gln Gln Leu Pro Gly Thr Ala Pro Lys Leu Leu
35 40 45

Ile Tyr Leu Asn Asp Arg Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Phe Trp Asp Asp His Leu
85 90 95

Lys Gly Trp Val Phe Gly Gly Gly Thr Lys Leu Thr Val Leu
100 105 110

<210> SEQ ID NO 92
<211> LENGTH: 110
<212> TYPE: PRT
<213> ORGANISM: Gallus gallus

<400> SEQUENCE: 92

Gln Ser Val Leu Thr Gln Pro Pro Ser Ala Ser Gly Thr Pro Gly Gln
1 5 10 15

Arg Val Thr Ile Ser Cys Ser Gly Val Thr Ser Asn Ile Ala Ser Tyr
20 25 30

His Val Tyr Trp Tyr Gln Gln Leu Pro Gly Thr Ala Pro Lys Leu Leu
35 40 45

Ile Tyr Leu Asn Ser Gln Arg Pro Ser Gly Val Pro Asp Arg Phe Ser
50 55 60

Ala Ser Lys Ser Gly Thr Ser Ala Ser Leu Ala Ile Ser Gly Leu Gln
65 70 75 80

Ser Glu Asp Glu Ala Asp Tyr Tyr Cys Ala Thr Trp Asp Gly Ser Gln
85 90 95

Asn Gly Trp Val Phe Gly Gly Gly Thr Lys Leu Thr Val Leu
100 105 110

<210> SEQ ID NO 93
<211> LENGTH: 116
<212> TYPE: PRT
<213> ORGANISM: Gallus gallus

<400> SEQUENCE: 93

Gln Ser Val Leu Thr Gln Pro Ser Ser Ala Ser Gly Thr Pro Gly Gln
1 5 10 15

Arg Val Thr Ile Ser Cys Ser Gly Thr Ile Ser Asn Ile Glu Thr Lys
20 25 30

Tyr Val Ser Trp Tyr Lys Tyr Val Ser Trp Tyr Gln Gln Leu Pro Gly
35 40 45

Thr Ala Pro Lys Leu Leu Ile Tyr Asn Asn Val Gln Arg Pro Ser Gly
50 55 60

Val Pro Asp Arg Phe Ser Gly Ser Gln Ser Gly Thr Ser Ala Ser Leu
65 70 75 80

Ala Ile Ser Gly Leu Gln Ser Glu Asp Glu Ala His Tyr Tyr Cys Ala
85 90 95

Ser Trp Glu Gly Gly Leu Asn Ser Trp Val Phe Gly Gly Gly Thr Lys
100 105 110

Leu Thr Val Leu
115

<210> SEQ ID NO 94
<211> LENGTH: 110
<212> TYPE: PRT
<213> ORGANISM: Gallus gallus

<400> SEQUENCE: 94

Gln Ser Val Leu Thr Gln Pro Pro Ser Ala Ser Gly Thr Pro Gly Gln
1 5 10 15

Arg Val Thr Ile Ser Cys Ser Ala Ser Asn Ser Tyr Ile Gly Thr Lys
20 25 30

Tyr Phe Tyr Trp Tyr Gln Gln Leu Pro Gly Thr Ala Pro Lys Leu Leu
35 40 45

Ile Tyr Leu Asp Ser Gln Arg Pro Ser Gly Val Pro Asp Arg Phe Ser
50 55 60

Gly Ser Lys Ser Gly Thr Ser Val Ser Leu Ala Ile Ser Gly Leu Gln
65 70 75 80

Ser Glu Asp Glu Ala Asp Tyr Tyr Cys Ala Phe Trp Asp Asp His Leu
85 90 95

His Gly Trp Val Phe Gly Gly Gly Thr Lys Leu Thr Val Leu
100 105 110

<210> SEQ ID NO 95
<211> LENGTH: 110
<212> TYPE: PRT
<213> ORGANISM: Gallus gallus

<400> SEQUENCE: 95

Gln Ser Gly Leu Thr Gln Pro Pro Ser Ala Ser Gly Thr Pro Gly Gln
1 5 10 15

Arg Val Thr Ile Ser Cys Ser Gly Asp Ile Ser Asn Thr Arg Asn Asn
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Ala Thr Ser Ala Ser Leu Ala Ile Ser Gly Leu Gln
65 70 75 80

Ser Glu Asp Glu Ala Asp Tyr His Cys Gly Thr Trp Asp Asn Thr Leu
85 90 95

Asn Ala Trp Val Phe Gly Gly Gly Thr Lys Leu Thr Val Leu
100 105 110

<210> SEQ ID NO 96
<211> LENGTH: 110
<212> TYPE: PRT
<213> ORGANISM: Gallus gallus

<400> SEQUENCE: 96

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Arg Asn Asn
20 25 30

Phe Val Ser Trp Tyr Gln His Leu Pro Gly Met Ala Pro Lys Leu Leu
35 40 45

Ile Tyr Gly Asn Ser Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Phe Ser Val
85 90 95

Asn Gly Trp Val Phe Gly Gly Gly Thr Lys Leu Thr Val Leu
100 105 110

<210> SEQ ID NO 97
<211> LENGTH: 110
<212> TYPE: PRT
<213> ORGANISM: Gallus gallus

<400> SEQUENCE: 97

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Arg Asn Asn
20 25 30

Phe Val Ser Trp Tyr Gln His Leu Pro Gly Thr Ala Pro Lys Leu Leu
35 40 45

Ile Tyr Gly Asn Ser Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Phe Ser Val
85 90 95

Ser Gly Trp Val Phe Gly Gly Gly Thr Lys Leu Thr Val Leu
100 105 110

<210> SEQ ID NO 98
<211> LENGTH: 110
<212> TYPE: PRT
<213> ORGANISM: Gallus gallus

<400> SEQUENCE: 98

Gln Ser Gly Leu Thr Gln Pro Pro Ser Ala Ser Gly Thr Pro Gly Gln
1 5 10 15

Arg Val Thr Ile Ser Cys Ser Gly Asp Ile Ser Asn Thr Arg Asn Asn
20 25 30

Tyr Val Ser Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Ala Thr Ser Ala Ser Leu Ala Ile Ser Gly Leu Gln
65 70 75 80

Ser Glu Asp Glu Ala Asp Tyr Tyr Cys Gly Thr Trp Asp Asn Thr Leu
85 90 95

Asn Ala Trp Val Phe Gly Gly Gly Thr Lys Leu Thr Val Leu
100 105 110

<210> SEQ ID NO 99
<211> LENGTH: 110
<212> TYPE: PRT
<213> ORGANISM: Gallus gallus

<400> SEQUENCE: 99

Gln Ser Val Leu Thr Gln Pro Pro Ser Ala Ser Gly Thr Pro Gly Gln
1 5 10 15

Arg Val Ile Ile Ser Cys Ser Gly Thr Asn Ser Asn Ile Gly Ser Asn
20 25 30

His Val Asn Trp Tyr Gln Gln Leu Pro Gly Thr Ala Pro Lys Leu Leu
35 40 45

Ile Tyr Thr Asn Asn Gln Arg Pro Ser Gly Val Pro Asp Arg Phe Ser
50 55 60

Gly Ser Ala Ser Gly Thr Ser Ala Ser Leu Ala Ile Ser Gly Val Gln
65 70 75 80

Ser Glu Asp Glu Ala Asp Tyr Tyr Cys Ala Ala Trp Asp Gly Ser Leu
85 90 95

```
Asn Gly Trp Val Phe Gly Gly Gly Thr Lys Leu Thr Val Leu
            100                 105                 110


<210> SEQ ID NO 100
<211> LENGTH: 110
<212> TYPE: PRT
<213> ORGANISM: Gallus gallus

<400> SEQUENCE: 100

Gln Ser Gly Leu Thr Gln Pro Pro Ser Ala Ser Gly Thr Pro Gly Gln
1               5                   10                  15

Arg Val Thr Ile Ser Cys Ser Gly Asp Ile Ser Asn Thr Arg Asn Asn
            20                  25                  30

Tyr Val Ser Trp Tyr Gln Gln Leu Pro Gly Thr Ala Pro Lys Leu Leu
        35                  40                  45

Ile Tyr Gly Asn His Gln Arg Pro Ser Gly Val Pro Asp Arg Phe Ser
    50                  55                  60

Gly Ser Lys Ser Ala Thr Ser Ala Ser Leu Ala Ile Ser Gly Leu Gln
65                  70                  75                  80

Ser Glu Asp Glu Ala Asp Tyr Tyr Cys Gly Thr Trp Asp Asn Thr Leu
                85                  90                  95

Asn Ala Trp Val Phe Gly Gly Gly Thr Lys Leu Thr Val Leu
            100                 105                 110


<210> SEQ ID NO 101
<211> LENGTH: 110
<212> TYPE: PRT
<213> ORGANISM: Gallus gallus

<400> SEQUENCE: 101

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Val Gly Asp His
            20                  25                  30

Tyr Val His Trp Tyr Gln Gln Leu Pro Gly Thr Ala Pro Lys Leu Leu
        35                  40                  45

Ile Tyr Lys Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Thr Trp Asp Asn Thr Leu
                85                  90                  95

Asn Gly Trp Val Phe Gly Gly Gly Thr Lys Leu Thr Val Leu
            100                 105                 110


<210> SEQ ID NO 102
<211> LENGTH: 110
<212> TYPE: PRT
<213> ORGANISM: Gallus gallus

<400> SEQUENCE: 102

Gln Ser Val Leu Thr Gln Pro Pro Ser Ala Ser Gly Thr Pro Gly Gln
1               5                   10                  15

Arg Val Ile Ile Ser Cys Ser Gly Thr Asn Ser Asn Ile Gly Ser Asn
            20                  25                  30

His Val Asn Trp Tyr Gln Gln Leu Pro Gly Thr Ala Pro Lys Leu Leu
        35                  40                  45
```

Ile Tyr Thr Asn Asn Gln Arg Pro Ser Gly Val Pro Asp Arg Phe Ser
50 55 60

Gly Ser Ala Ser Gly Thr Ser Ala Ser Leu Ala Ile Ser Gly Val Gln
65 70 75 80

Ser Glu Asp Glu Ala Asp Tyr Tyr Cys Ala Ala Trp Asp Gly Ser Leu
85 90 95

Asn Gly Trp Val Phe Gly Gly Gly Thr Lys Leu Thr Val Leu
100 105 110

<210> SEQ ID NO 103
<211> LENGTH: 110
<212> TYPE: PRT
<213> ORGANISM: Gallus gallus

<400> SEQUENCE: 103

Gln Ser Val Leu Thr Gln Pro Pro Ser Ala Ser Gly Thr Pro Gly Gln
1 5 10 15

Arg Val Thr Ile Ser Cys Ser Gly Val Thr Ser Asn Ile Arg Asn Ser
20 25 30

Tyr Val Ser Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Gly Thr Trp Asp Asn Thr Leu
85 90 95

Asn Ala Trp Val Phe Gly Gly Gly Thr Lys Leu Thr Val Leu
100 105 110

<210> SEQ ID NO 104
<211> LENGTH: 110
<212> TYPE: PRT
<213> ORGANISM: Gallus gallus

<400> SEQUENCE: 104

Gln Ser Val Leu Thr Gln Pro Pro Ser Ala Ser Gly Thr Pro Gly Gln
1 5 10 15

Arg Val Thr Ile Ser Cys Ser Gly Ser Asn Ser Asn Ile Arg Asn Asn
20 25 30

Phe Val Ser Trp Tyr Gln His Leu Pro Gly Thr Ala Pro Lys Leu Leu
35 40 45

Ile Tyr Gly Asn Ser Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Thr Ser Trp Asp Phe Ser Val
85 90 95

Asn Gly Trp Val Phe Gly Gly Gly Thr Lys Leu Thr Val Leu
100 105 110

<210> SEQ ID NO 105
<211> LENGTH: 110
<212> TYPE: PRT
<213> ORGANISM: Gallus gallus

<400> SEQUENCE: 105

Gln Ser Gly Leu Thr Gln Pro Pro Ser Ala Ser Gly Thr Pro Gly Gln
1 5 10 15

Arg Val Thr Ile Ser Cys Ser Gly Asp Ile Ser Asn Thr Arg Asn Asn
20 25 30

Tyr Val Ser Trp Tyr Gln Gln Leu Pro Gly Thr Ala Pro Lys Leu Leu
35 40 45

Ile Tyr Arg Asn Ser Gln Arg Pro Ser Gly Val Pro Asp Arg Phe Ser
50 55 60

Gly Ser Lys Ser Ala Thr Ser Ala Ser Leu Ala Ile Ser Gly Leu Gln
65 70 75 80

Ser Glu Asp Glu Ala Asp Tyr Tyr Cys Gly Thr Trp Asp Asn Thr Leu
85 90 95

Asn Ala Trp Val Phe Gly Gly Gly Thr Lys Leu Thr Val Leu
100 105 110

<210> SEQ ID NO 106
<211> LENGTH: 110
<212> TYPE: PRT
<213> ORGANISM: Gallus gallus

<400> SEQUENCE: 106

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gln Ser Asn
20 25 30

Tyr Val Tyr Trp Tyr Gln Gln Leu Pro Gly Thr Ala Pro Lys Leu Leu
35 40 45

Ile Tyr Gly Asn His Gln Arg Pro Ser Gly Val Pro Asp Arg Phe Ser
50 55 60

Gly Ser Lys Ser Asp Thr Ser Ala Ser Leu Ala Ile Ser Gly Leu Gln
65 70 75 80

Ser Glu Asp Glu Ala Asp Tyr Tyr Cys Ala Thr Trp Asp Ala Ser Leu
85 90 95

Asn Val Trp Val Phe Gly Gly Gly Thr Lys Leu Thr Val Leu
100 105 110

<210> SEQ ID NO 107
<211> LENGTH: 110
<212> TYPE: PRT
<213> ORGANISM: Gallus gallus

<400> SEQUENCE: 107

Gln Ser Val Leu Thr Gln Pro Pro Ser Ala Ser Gly Thr Pro Gly Gln
1 5 10 15

Arg Val Thr Ile Ser Cys Ser Gly Val Thr Ser Asn Ile Arg Asn Tyr
20 25 30

Tyr Val Ser Trp Tyr Gln Gln Leu Pro Gly Thr Ala Pro Lys Leu Leu
35 40 45

Ile Tyr Gly Asn Asp Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Gly Thr Trp Asp Asn Thr Leu
85 90 95

Asn Ala Trp Val Phe Gly Gly Gly Thr Lys Leu Thr Val Leu
100 105 110

<210> SEQ ID NO 108
<211> LENGTH: 109
<212> TYPE: PRT
<213> ORGANISM: Gallus gallus

<400> SEQUENCE: 108

Gln Ser Val Leu Thr Gln Pro Pro Ser Val Ser Gly Thr Pro Gly Gln
1 5 10 15

Arg Val Thr Ile Ser Cys Ser Gly Thr Ile Ser Asn Val Gly Asn Lys
20 25 30

Tyr Val Ser Trp Tyr Gln Gln Val Pro Gly Thr Ala Pro Lys Leu Leu
35 40 45

Ile Asp Tyr Asn Gln Arg Pro Ser Gly Val Pro Asp Arg Phe Ser Gly
50 55 60

Ser Gln Ser Gly Thr Ser Ala Ser Leu Thr Ile Ser Gly Leu Gln Ser
65 70 75 80

Glu Asp Glu Ala Asp Tyr Tyr Cys Ala Thr Trp Asp Asp Ser Leu Lys
85 90 95

Gly Trp Val Phe Gly Gly Gly Thr Lys Leu Thr Val Leu
100 105

<210> SEQ ID NO 109
<211> LENGTH: 7
<212> TYPE: PRT
<213> ORGANISM: Gallus gallus

<400> SEQUENCE: 109

Gly Phe Thr Phe Asp Asp Tyr
1 5

<210> SEQ ID NO 110
<211> LENGTH: 6
<212> TYPE: PRT
<213> ORGANISM: Gallus gallus

<400> SEQUENCE: 110

Asn Trp Asn Gly Asp Lys
1 5

<210> SEQ ID NO 111
<211> LENGTH: 11
<212> TYPE: PRT
<213> ORGANISM: Gallus gallus

<400> SEQUENCE: 111

His Trp Ile Val Phe Gln Tyr Gly Met Asp Val
1 5 10

<210> SEQ ID NO 112
<211> LENGTH: 7
<212> TYPE: PRT
<213> ORGANISM: Gallus gallus

<400> SEQUENCE: 112

Gly Phe Thr Phe Asp Asp Tyr
1 5

<210> SEQ ID NO 113
<211> LENGTH: 6

<212> TYPE: PRT
<213> ORGANISM: Gallus gallus

<400> SEQUENCE: 113

Asn Trp Asn Gly Asp Lys
1 5

<210> SEQ ID NO 114
<211> LENGTH: 11
<212> TYPE: PRT
<213> ORGANISM: Gallus gallus

<400> SEQUENCE: 114

His Trp Ile Val Phe Gln Tyr Gly Leu Asp Val
1 5 10

<210> SEQ ID NO 115
<211> LENGTH: 7
<212> TYPE: PRT
<213> ORGANISM: Gallus gallus

<400> SEQUENCE: 115

Gly Phe Thr Phe Thr Ser Tyr
1 5

<210> SEQ ID NO 116
<211> LENGTH: 6
<212> TYPE: PRT
<213> ORGANISM: Gallus gallus

<400> SEQUENCE: 116

Thr Trp Asp Gly Asp Arg
1 5

<210> SEQ ID NO 117
<211> LENGTH: 11
<212> TYPE: PRT
<213> ORGANISM: Gallus gallus

<400> SEQUENCE: 117

His Trp Thr Val Phe Gln Tyr Gly Met Asp Val
1 5 10

<210> SEQ ID NO 118
<211> LENGTH: 7
<212> TYPE: PRT
<213> ORGANISM: Gallus gallus

<400> SEQUENCE: 118

Gly Phe Thr Phe Ser Asp Tyr
1 5

<210> SEQ ID NO 119
<211> LENGTH: 6
<212> TYPE: PRT
<213> ORGANISM: Gallus gallus

<400> SEQUENCE: 119

Thr Trp Asp Gly Asp Arg
1 5

<210> SEQ ID NO 120
<211> LENGTH: 11
<212> TYPE: PRT
<213> ORGANISM: Gallus gallus

<400> SEQUENCE: 120

His Trp Thr Val Phe Gln Tyr Gly Met Asp Val
1 5 10

<210> SEQ ID NO 121
<211> LENGTH: 7
<212> TYPE: PRT
<213> ORGANISM: Gallus gallus

<400> SEQUENCE: 121

Gly Phe Thr Phe Ile Asp Phe
1 5

<210> SEQ ID NO 122
<211> LENGTH: 6
<212> TYPE: PRT
<213> ORGANISM: Gallus gallus

<400> SEQUENCE: 122

Ser Trp Ile Gly Asp Thr
1 5

<210> SEQ ID NO 123
<211> LENGTH: 11
<212> TYPE: PRT
<213> ORGANISM: Gallus gallus

<400> SEQUENCE: 123

His Trp Thr Val Tyr Gln Tyr Gly Met Asp Val
1 5 10

<210> SEQ ID NO 124
<211> LENGTH: 7
<212> TYPE: PRT
<213> ORGANISM: Gallus gallus

<400> SEQUENCE: 124

Gly Phe Thr Phe Ser Ser Tyr
1 5

<210> SEQ ID NO 125
<211> LENGTH: 5
<212> TYPE: PRT
<213> ORGANISM: Gallus gallus

<400> SEQUENCE: 125

His Ile Ser Asp Ser
1 5

<210> SEQ ID NO 126
<211> LENGTH: 11
<212> TYPE: PRT
<213> ORGANISM: Gallus gallus

<400> SEQUENCE: 126

Gly His Thr Val Leu Gln Tyr Gly Met Asp Val
1 5 10

<210> SEQ ID NO 127
<211> LENGTH: 7
<212> TYPE: PRT
<213> ORGANISM: Gallus gallus

<400> SEQUENCE: 127

Gly Phe Thr Phe Ser Ser Tyr
1 5

<210> SEQ ID NO 128
<211> LENGTH: 7
<212> TYPE: PRT
<213> ORGANISM: Gallus gallus

<400> SEQUENCE: 128

Ser Ile Phe Ser Gly Asp Ser
1 5

<210> SEQ ID NO 129
<211> LENGTH: 11
<212> TYPE: PRT
<213> ORGANISM: Gallus gallus

<400> SEQUENCE: 129

Ser His Thr Val Leu Gln Tyr Gly Met Asp Val
1 5 10

<210> SEQ ID NO 130
<211> LENGTH: 7
<212> TYPE: PRT
<213> ORGANISM: Gallus gallus

<400> SEQUENCE: 130

Gly Phe Ser Phe Trp Gly Tyr
1 5

<210> SEQ ID NO 131
<211> LENGTH: 5
<212> TYPE: PRT
<213> ORGANISM: Gallus gallus

<400> SEQUENCE: 131

Ala Gly Asn Ser Tyr
1 5

<210> SEQ ID NO 132
<211> LENGTH: 12
<212> TYPE: PRT
<213> ORGANISM: Gallus gallus

<400> SEQUENCE: 132

Asp Arg Ser Phe Tyr Asn Tyr Tyr Asp Ile Asp Val
1 5 10

<210> SEQ ID NO 133
<211> LENGTH: 14
<212> TYPE: PRT
<213> ORGANISM: Gallus gallus

<400> SEQUENCE: 133

Ser Gly Ser Ile Ser Asn Ile Glu Thr Lys Tyr Val Ser Trp
1 5 10

<210> SEQ ID NO 134
<211> LENGTH: 7
<212> TYPE: PRT
<213> ORGANISM: Gallus gallus

<400> SEQUENCE: 134

Asn Ser Asp Gln Arg Pro Ser
1 5

<210> SEQ ID NO 135
<211> LENGTH: 10
<212> TYPE: PRT
<213> ORGANISM: Gallus gallus

<400> SEQUENCE: 135

Val Ser Trp Asp Ala Ser Leu Lys Ser Trp
1 5 10

<210> SEQ ID NO 136
<211> LENGTH: 14
<212> TYPE: PRT
<213> ORGANISM: Gallus gallus

<400> SEQUENCE: 136

Ser Gly Val Ser Ser Asn Ile Glu Ile Lys Tyr Val Ser Trp
1 5 10

<210> SEQ ID NO 137
<211> LENGTH: 7
<212> TYPE: PRT
<213> ORGANISM: Gallus gallus

<400> SEQUENCE: 137

Asn Ser His Gln Arg Pro Ser
1 5

<210> SEQ ID NO 138
<211> LENGTH: 10
<212> TYPE: PRT
<213> ORGANISM: Gallus gallus

<400> SEQUENCE: 138

Thr Ser Trp Asp Asp Arg Leu Lys Ser Trp
1 5 10

<210> SEQ ID NO 139
<211> LENGTH: 14
<212> TYPE: PRT
<213> ORGANISM: Gallus gallus

<400> SEQUENCE: 139

Ser Gly Thr Ile Ser Asn Ile Glu Thr Lys Tyr Val Ser Trp
1 5 10

<210> SEQ ID NO 140
<211> LENGTH: 7
<212> TYPE: PRT
<213> ORGANISM: Gallus gallus

<400> SEQUENCE: 140

Gly Asn His Gln Arg Pro Ser
1 5

<210> SEQ ID NO 141
<211> LENGTH: 10
<212> TYPE: PRT
<213> ORGANISM: Gallus gallus

<400> SEQUENCE: 141

Ala Ser Trp Glu Asn Asp Leu Lys Ser Trp
1 5 10

<210> SEQ ID NO 142
<211> LENGTH: 14
<212> TYPE: PRT
<213> ORGANISM: Gallus gallus

<400> SEQUENCE: 142

Ser Gly Thr Ile Ser Asn Ile Glu Ile Lys Tyr Val Ser Trp
1 5 10

<210> SEQ ID NO 143
<211> LENGTH: 7
<212> TYPE: PRT
<213> ORGANISM: Gallus gallus

<400> SEQUENCE: 143

Gly Asn His Gln Arg Pro Ser
1 5

<210> SEQ ID NO 144
<211> LENGTH: 10
<212> TYPE: PRT
<213> ORGANISM: Gallus gallus

<400> SEQUENCE: 144

Ser Ser Trp Glu Asn Asp Leu Lys Ser Trp
1 5 10

<210> SEQ ID NO 145
<211> LENGTH: 14
<212> TYPE: PRT
<213> ORGANISM: Gallus gallus

<400> SEQUENCE: 145

Ser Gly Ser Thr Ser Asp Ile Glu Thr Lys Tyr Val Ser Trp
1 5 10

<210> SEQ ID NO 146
<211> LENGTH: 7
<212> TYPE: PRT
<213> ORGANISM: Gallus gallus

<400> SEQUENCE: 146

Gly Asn His Gln Arg Pro Ser
1 5

<210> SEQ ID NO 147
<211> LENGTH: 10
<212> TYPE: PRT
<213> ORGANISM: Gallus gallus

<400> SEQUENCE: 147

Thr Ala Trp Asp Asn Thr Leu Lys Ser Trp
1 5 10

<210> SEQ ID NO 148
<211> LENGTH: 14
<212> TYPE: PRT
<213> ORGANISM: Gallus gallus

<400> SEQUENCE: 148

Ser Gly Asp Ile Ser Asn Thr Arg Asn Asn Tyr Val Ser Trp
1 5 10

<210> SEQ ID NO 149
<211> LENGTH: 7
<212> TYPE: PRT
<213> ORGANISM: Gallus gallus

<400> SEQUENCE: 149

Gly Asn His Gln Arg Pro Ser
1 5

<210> SEQ ID NO 150
<211> LENGTH: 10
<212> TYPE: PRT
<213> ORGANISM: Gallus gallus

<400> SEQUENCE: 150

Gly Thr Trp Asp Asn Thr Leu Asn Ala Trp
1 5 10

<210> SEQ ID NO 151
<211> LENGTH: 14
<212> TYPE: PRT
<213> ORGANISM: Gallus gallus

<400> SEQUENCE: 151

Ser Gly Val Thr Ser Asn Ile Arg Asn Tyr Tyr Val Ser Trp
1 5 10

<210> SEQ ID NO 152
<211> LENGTH: 7
<212> TYPE: PRT
<213> ORGANISM: Gallus gallus

<400> SEQUENCE: 152

Gly Asn Asp Gln Arg Pro Ser
1 5

<210> SEQ ID NO 153
<211> LENGTH: 10
<212> TYPE: PRT
<213> ORGANISM: Gallus gallus

<400> SEQUENCE: 153

Gly Thr Trp Asp Asn Thr Leu Asn Ala Trp
1 5 10

<210> SEQ ID NO 154
<211> LENGTH: 14
<212> TYPE: PRT
<213> ORGANISM: Gallus gallus

<400> SEQUENCE: 154

Ser Gly Thr Asn Ser Asn Ile Gly Ser Asn His Val Asn Trp
1 5 10

<210> SEQ ID NO 155
<211> LENGTH: 7
<212> TYPE: PRT
<213> ORGANISM: Gallus gallus

```
<400> SEQUENCE: 155

Thr Asn Asn Gln Arg Pro Ser
1               5


<210> SEQ ID NO 156
<211> LENGTH: 10
<212> TYPE: PRT
<213> ORGANISM: Gallus gallus

<400> SEQUENCE: 156

Ala Ala Trp Asp Gly Ser Leu Asn Gly Trp
1               5                   10
```